United States Patent
Fujio et al.

(10) Patent No.: US 8,309,573 B2
(45) Date of Patent: Nov. 13, 2012

(54) SALT OF ISOQUINOLINE COMPOUND AND CRYSTAL THEREOF

(75) Inventors: Masakazu Fujio, Osaka (JP); Toshihiko Tanaka, Osaka (JP); Hisao Takayanagi, Osaka (JP); Hiroyuki Satoh, Osaka (JP); Takanori Ito, Osaka (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 468 days.

(21) Appl. No.: 12/672,784

(22) PCT Filed: Aug. 8, 2008

(86) PCT No.: PCT/JP2008/064289
§ 371 (c)(1),
(2), (4) Date: Feb. 9, 2010

(87) PCT Pub. No.: WO2009/022642
PCT Pub. Date: Feb. 19, 2009

(65) Prior Publication Data
US 2011/0130419 A1    Jun. 2, 2011

(30) Foreign Application Priority Data
Aug. 10, 2007  (JP) .................................. 2007/208693

(51) Int. Cl.
*A61K 31/47* (2006.01)
*C07D 217/22* (2006.01)

(52) U.S. Cl. ......................................... 514/309; 546/141
(58) Field of Classification Search .................. 514/309; 546/141
See application file for complete search history.

(56) References Cited

U.S. PATENT DOCUMENTS
7,220,759 B2    5/2007  Fujio et al.

FOREIGN PATENT DOCUMENTS
WO    WO 2004/031171 A1    4/2004

OTHER PUBLICATIONS

Anderson and Flora, "Preparation of Water-Soluble Compounds Through Salt Formation" (Chapter 34 at pp. 739-754) in *The Practice of Medicinal Chemistry*, Camille Georges Wermuth, editor (Academic Press 1996) [translated into the Japanese language under the supervision of Hiroshi Nagase, Saishin Soyaku Kagaku Gekan, Technomics, Inc.(Sep. 25, 1999), pp. 347-365 of Japanese text].

*Primary Examiner* — Rebecca Anderson
(74) *Attorney, Agent, or Firm* — Leydig, Voit & Mayer, Ltd.

(57) ABSTRACT

The invention provides a salt of (R)-3-[2-(2-hydroxymethylpyrrolidin-1-yl)ethyl]-5-methyl-2H-isoquinolin-1-one and a crystal thereof. (R)-3-[2-(2-Hydroxymethylpyrrolidin-1-ypethyl]-5-methyl-2H-1-isoquinolin-1-one monophosphate is a compound which is chemically stable, has high solubility, and shows less weight change due to humidity as compared to a free form and monohydrochloride dihydrate, and is superior as a bulk drug for pharmaceutical products.

35 Claims, 17 Drawing Sheets

SALT OF ISOQUINOLINE COMPOUND AND CRYSTAL THEREOF

TECHNICAL FIELD

The present invention relates to a salt of (R)-3-[2-(2-hydroxymethylpyrrolidin-1-yl)ethyl]-5-methyl-2H-isoquinolin-1-one and a crystal thereof, and a pharmaceutical use thereof.

BACKGROUND ART (R)-3-[2-(2-Hydroxymethylpyrrolidin-1-yl)ethyl]-5-methyl-2H-isoquinolin-1-one and hydrochloride dihydrate thereof is a compound described in Example 36 of WO 2004/031171 (patent document 1). This compound possesses a potent poly(ADP-ribose)polymerase (Poly(ADP-ribose)polymerase; hereinafter to be abbreviated as "PARP") inhibitory action, and is useful for the treatment or prophylaxis of cerebral infarction.

While a free form and hydrochloride dihydrate of the aforementioned compound are described in Example 36 of patent document 1, other salt forms are not specifically described.
patent document 1: WO 2004/031171

DISCLOSURE OF THE INVENTION

Problems to be Solved by the Invention

The problem of the present invention is to provide a novel salt form of (R)-3-[2-(2-hydroxymethylpyrrolidin-1-yl)ethyl]-5-methyl-2H-isoquinolin-1-one.

Means of Solving the Problems

In view of the above-mentioned problem, the present inventors have conducted intensive studies and found that, from among the compounds of the present invention, (R)-3-[2-(2-hydroxymethylpyrrolidin-1-yl)ethyl]-5-methyl-2H-isoquinolin-1-one monophosphate (hereinafter sometimes to be simply indicated as monophosphate) is particularly superior in the chemical stability and has high solubility as compared to its free form, as well as shows low hygroscopicity and has high solubility as compared to (R)-3-[2-(2-hydroxymethylpyrrolidin-1-yl)ethyl]-5-methyl-2H-isoquinolin-1-one hydrochloride dihydrate, which resulted in the completion of the present invention.

Accordingly, the present invention provides the following.
(1) (R)-3-[2-(2-Hydroxymethylpyrrolidin-1-yl)ethyl]-5-methyl-2H-isoquinolin-1-one monophosphate.
(2) The (R)-3-[2-(2-hydroxymethylpyrrolidin-1-yl)ethyl]-5-methyl-2H-isoquinolin-1-one monophosphate described above, which is an anhydrate.
(3) The (R)-3-[2-(2-hydroxymethylpyrrolidin-1-yl)ethyl]-5-methyl-2H-isoquinolin-1-one monophosphate described above, which is a crystal.
(4) An anhydrous crystal of (R)-3-[2-(2-hydroxymethylpyrrolidin-1-yl)ethyl]-5-methyl-2H-isoquinolin-1-one monophosphate.
(5) The crystal described above showing a powder X-ray diffraction spectrum having a peak at a diffraction angle represented by 2θ of around 12.0° (±0.2°).
(6) The crystal described above showing a powder X-ray diffraction spectrum having a peak at a diffraction angle represented by 2θ of around 22.8° (±0.2°).
(7) The crystal described above showing a powder X-ray diffraction spectrum having a peak at a diffraction angle represented by 2θ of around 15.0° (±0.2°).
(8) The crystal described above showing a powder X-ray diffraction spectrum having a peak at a diffraction angle represented by 2θ of around 19.6° (±0.2°).
(9) The crystal described above showing a powder X-ray diffraction spectrum having a peak at a diffraction angle represented by 2θ of around 25.8° (±0.2°).
(10) The crystal described above showing a powder X-ray diffraction spectrum having a peak at a diffraction angle represented by 2θ of around 17.8° (±0.2°).
(11) The crystal described above showing a powder X-ray diffraction spectrum having peaks at diffraction angles represented by 2θ of around 12.0°, 15.0°, 17.8°, 19.6°, 20.0°, 22.8° and 25.8° (each ±0.2°).
(12) The crystal described above having a melting point (extrapolated onset temperature) by thermogravimetry-differential thermal analysis of about 216° C. to about 217° C.
(13) The crystal described above having a melting point (extrapolated onset temperature) by thermogravimetry-differential thermal analysis of about 216° C.
(14) An anhydrous crystal of (R)-3-[2-(2-hydroxymethylpyrrolidin-1-yl)ethyl]-5-methyl-2H-isoquinolin-1-one monophosphate having physicochemical properties shown by the following A and/or B:
A: having a powder X-ray diffraction pattern shown in FIG. 3,
B: having a thermogravimetry-differential thermal analysis curve shown in FIG. 4.
(15) (R)-3-[2-(2-Hydroxymethylpyrrolidin-1-yl)ethyl]-5-methyl-2H-isoquinolin-1-one hemiphosphate.
(16) The (R)-3-[2-(2-hydroxymethylpyrrolidin-1-yl)ethyl]-5-methyl-2H-isoquinolin-1-one hemiphosphate described above, which is a monohydrate.
(17) The (R)-3-[2-(2-hydroxymethylpyrrolidin-1-yl)ethyl]-5-methyl-2H-isoquinolin-1-one hemiphosphate described above, which is a crystal.
(18) A crystal of (R)-3-[2-(2-hydroxymethylpyrrolidin-1-yl)ethyl]-5-methyl-2H-isoquinolin-1-one hemiphosphate monohydrate.
(19) The crystal described above showing a powder X-ray diffraction spectrum having peaks at diffraction angles represented by 2θ of around 8.8°, 11.8°, 14.4°, 21.4°, 23.7°, 24.6° and 26.6° (each ±0.2°).
(20) The crystal described above having a melting point (extrapolated onset temperature) by thermogravimetry-differential thermal analysis of about 199° C.
(21) A crystal of (R)-3-[2-(2-hydroxymethylpyrrolidin-1-yl)ethyl]-5-methyl-2H-isoquinolin-1-one hemiphosphate monohydrate having physicochemical properties shown by the following C and/or D:
C: having a powder X-ray diffraction pattern shown in FIG. 5,
D: having a thermogravimetry-differential thermal analysis curve shown in FIG. 6.
(22) (R)-3-[2-(2-Hydroxymethylpyrrolidin-1-yl)ethyl]-5-methyl-2H-isoquinolin-1-one diphosphate.
(23) The (R)-3-[2-(2-hydroxymethylpyrrolidin-1-yl)ethyl]-5-methyl-2H-isoquinolin-1-one diphosphate described above, which is a monohydrate 0.5 ethanol solvate.
(24) The (R)-3-[2-(2-hydroxymethylpyrrolidin-1-yl)ethyl]-5-methyl-2H-isoquinolin-1-one diphosphate described above, which is a crystal.
(25) A crystal of (R)-3-[2-(2-hydroxymethylpyrrolidin-1-yl)ethyl]-5-methyl-2H-isoquinolin-1-one diphosphate monohydrate 0.5 ethanol solvate.

(26) The crystal described above showing a powder X-ray diffraction spectrum having peaks at diffraction angles represented by 2θ of around 6.6°, 13.1°, 23.1° and 26.4° (each ±0.2°).

(27) The crystal described above having a melting point (extrapolated onset temperature) by thermogravimetry-differential thermal analysis of about 196° C.

(28) A crystal of (R)-3-[2-(2-hydroxymethylpyrrolidin-1-yl)ethyl]-5-methyl-2H-isoquinolin-1-one diphosphate monohydrate 0.5 ethanol solvate having physicochemical properties shown by the following E and/or F:

E: having a powder X-ray diffraction pattern shown in FIG. 7,
F: having a thermogravimetry-differential thermal analysis curve shown in FIG. 8.

(29) Anhydrous (R)-3-[2-(2-hydroxymethylpyrrolidin-1-yl)ethyl]-5-methyl-2H-isoquinolin-1-one monohydrochloride.

(30) An anhydrous crystal of (R)-3-[2-(2-hydroxymethylpyrrolidin-1-yl)ethyl]-5-methyl-2H-isoquinolin-1-one monohydrochloride.

(31) The crystal described above showing a powder X-ray diffraction spectrum having peaks at diffraction angles represented by 2θ of around 6.7°, 21.8° and 30.2° (each ±0.2°).

(32) The crystal described above having a melting point (extrapolated onset temperature) by thermogravimetry-differential thermal analysis of about 110° C.

(33) An anhydrous crystal of (R)-3-[2-(2-hydroxymethylpyrrolidin-1-yl)ethyl]-5-methyl-2H-isoquinolin-1-one monohydrochloride having physicochemical property shown by the following G:

G: having a powder X-ray diffraction pattern shown in FIG. 9.

(34) The crystal described above showing a powder X-ray diffraction spectrum having peaks at diffraction angles represented by 2θ of around 15.5°, 29.4°, 31.4°, 31.9° and 34.3° (each ±0.2°).

(35) The crystal described above having a melting point (extrapolated onset temperature) by thermogravimetry-differential thermal analysis of about 231° C.

(36) An anhydrous crystal of (R)-3-[2-(2-hydroxymethylpyrrolidin-1-yl)ethyl]-5-methyl-2H-isoquinolin-1-one monohydrochloride having physicochemical property shown by the following H:

H: having a powder X-ray diffraction pattern shown in FIG. 10.

(37) The crystal described above showing a powder X-ray diffraction spectrum having peaks at diffraction angles represented by 2θ of around 9.1°, 19.8°, 20.9° and 28.6° (each ±0.2°).

(38) The crystal described above having a melting point (extrapolated onset temperature) by thermogravimetry-differential thermal analysis of about 208° C.

(39) An anhydrous crystal of (R)-3-[2-(2-hydroxymethylpyrrolidin-1-yl)ethyl]-5-methyl-2H-isoquinolin-1-one monohydrochloride having physicochemical properties shown by the following I and/or J:

I: having a powder X-ray diffraction pattern shown in FIG. 11,
J: having a thermogravimetry-differential thermal analysis curve shown in FIG. 12.

(40) Anhydrous (R)-3-[2-(2-hydroxymethylpyrrolidin-1-yl)ethyl]-5-methyl-2H-isoquinolin-1-one monohydrobromide.

(41) An anhydrous crystal of (R)-3-[2-(2-hydroxymethylpyrrolidin-1-yl)ethyl]-5-methyl-2H-isoquinolin-1-10 one monohydrobromide.

(42) The crystal described above showing a powder X-ray diffraction spectrum having peaks at diffraction angles represented by 2θ of around 11.0°, 12.8° and 20.3° (each ±0.2°).

(43) The crystal described above having a melting point (extrapolated onset temperature) by thermogravimetry-differential thermal analysis of about 173° C.

(44) An anhydrous crystal of (R)-3-[2-(2-hydroxymethylpyrrolidin-1-yl)ethyl]-5-methyl-2H-isoquinolin-1-one monohydrobromide having physicochemical properties shown by the following K and/or L:

K: having a powder X-ray diffraction pattern shown in FIG. 15,
L: having a thermogravimetry-differential thermal analysis curve shown in FIG. 16.

(45) The crystal described above showing a powder X-ray diffraction spectrum having peaks at diffraction angles represented by 2θ of around 8.3°, 9.2° and 14.0° (each ±0.2°).

(46) The crystal described above having a melting point (extrapolated onset temperature) by thermogravimetry-differential thermal analysis of about 235° C.

(47) An anhydrous crystal of (R)-3-[2-(2-hydroxymethylpyrrolidin-1-yl)ethyl]-5-methyl-2H-isoquinolin-1-one monohydrobromide having physicochemical properties shown by the following M and/or N:

M: having a powder X-ray diffraction pattern shown in FIG. 17,
N: having a thermogravimetry-differential thermal analysis curve shown in FIG. 18.

(48) (R)-3-[2-(2-Hydroxymethylpyrrolidin-1-yl)ethyl]-5-methyl-2H-isoquinolin-1-one monohydrobromide.

(49) The (R)-3-[2-(2-hydroxymethylpyrrolidin-1-yl)ethyl]-5-methyl-2H-isoquinolin-1-one monohydrobromide described above, which is a dihydrate.

(50) The (R)-3-[2-(2-hydroxymethylpyrrolidin-1-yl)ethyl]-5-methyl-2H-isoquinolin-1-one monohydrobromide described above, which is a crystal.

(51) A crystal of (R)-3-[2-(2-hydroxymethylpyrrolidin-1-yl)ethyl]-5-methyl-2H-isoquinolin-1-one monohydrobromide dihydrate.

(52) The crystal described above showing a powder X-ray diffraction spectrum having peaks at diffraction angles represented by 2θ of around 11.7°, 17.4°, 21.1° and 26.0° (each ±0.2°).

(53) A crystal of (R)-3-[2-(2-hydroxymethylpyrrolidin-1-yl)ethyl]-5-methyl-2H-isoquinolin-1-one monohydrobromide dihydrate having physicochemical properties shown by the following O and/or P:

O: having a powder X-ray diffraction pattern shown in FIG. 19,
P: having a thermogravimetry-differential thermal analysis curve shown in FIG. 20.

(54) Anhydrous (R)-3-[2-(2-hydroxymethylpyrrolidin-1-yl)ethyl]-5-methyl-2H-isoquinolin-1-one monomesylate.

(55) An anhydrous crystal of (R)-3-[2-(2-hydroxymethylpyrrolidin-1-yl)ethyl]-5-methyl-2H-isoquinolin-1-one monomesylate.

(56) The crystal described above showing a powder X-ray diffraction spectrum having peaks at diffraction angles represented by 2θ of around 15.6° and 20.7° (each ±0.2°).

(57) The crystal described above having a melting point (extrapolated onset temperature) by thermogravimetry-differential thermal analysis of about 176° C.

(58) An anhydrous crystal of (R)-3-[2-(2-hydroxymethylpyrrolidin-1-yl)ethyl]-5-methyl-2H-isoquinolin-1-one monomesylate having physicochemical properties shown by the following Q and/or R:
Q: having a powder X-ray diffraction pattern shown in FIG. 21,
R: having a thermogravimetry-differential thermal analysis curve shown in FIG. 22.

(59) Anhydrous (R)-3-[2-(2-hydroxymethylpyrrolidin-1-yl)ethyl]-5-methyl-2H-isoquinolin-1-one hemisulfate.

(60) An anhydrous crystal of (R)-3-[2-(2-hydroxymethylpyrrolidin-1-yl)ethyl]-5-methyl-2H-isoquinolin-1-one hemisulfate.

(61) The crystal described above showing a powder X-ray diffraction spectrum having peaks at diffraction angles represented by 2θ of around 7.2°, 13.1° and 25.2° (each ±0.2°).

(62) The crystal described above having a melting point (extrapolated onset temperature) by thermogravimetry-differential thermal analysis of about 166° C.

(63) An anhydrous crystal of (R)-3-[2-(2-hydroxymethylpyrrolidin-1-yl)ethyl]-5-methyl-2H-isoquinolin-1-one hemisulfate having physicochemical properties shown by the following S and/or T:
S: having a powder X-ray diffraction pattern shown in FIG. 23,
T: having a thermogravimetry-differential thermal analysis curve shown in FIG. 24.

(64) (R)-3-[2-(2-Hydroxymethylpyrrolidin-1-yl)ethyl]-5-methyl-2H-isoquinolin-1-one hemisulfate.

(65) The (R)-3-[2-(2-hydroxymethylpyrrolidin-1-yl)ethyl]-5-methyl-2H-isoquinolin-1-one hemisulfate described above, which is a sesquihydrate.

(66) The (R)-3-[2-(2-hydroxymethylpyrrolidin-1-yl)ethyl]-5-methyl-2H-isoquinolin-1-one hemisulfate described above, which is a crystal.

(67) A crystal of (R)-3-[2-(2-hydroxymethylpyrrolidin-1-yl)ethyl]-5-methyl-2H-isoquinolin-1-one hemisulfate sesquihydrate.

(68) The crystal described above showing a powder X-ray diffraction spectrum having peaks at diffraction angles represented by 2θ of around 5.3°, 8.1°, 10.6° and 22.9° (each ±0.2°).

(69) The crystal described above having a melting point (extrapolated onset temperature) by thermogravimetry-differential thermal analysis of about 106° C.

(70) A crystal of (R)-3-[2-(2-hydroxymethylpyrrolidin-1-yl)ethyl]-5-methyl-2H-isoquinolin-1-one hemisulfate sesquihydrate having physicochemical properties shown by the following U and/or V:
U: having a powder X-ray diffraction pattern shown in FIG. 25,
V: having a thermogravimetry-differential thermal analysis curve shown in FIG. 26.

(71) Anhydrous (R)-3-[2-(2-hydroxymethylpyrrolidin-1-yl)ethyl]-5-methyl-2H-isoquinolin-1-one monosulfate.

(72) An anhydrous crystal of (R)-3-[2-(2-hydroxymethylpyrrolidin-1-yl)ethyl]-5-methyl-2H-isoquinolin-1-one monosulfate.

(73) The crystal described above showing a powder X-ray diffraction spectrum having peaks at diffraction angles represented by 2θ of around 12.2° and 21.7° (each ±0.2°).

(74) The crystal described above having a melting point (extrapolated onset temperature) by thermogravimetry-differential thermal analysis of about 176° C.

(75) An anhydrous crystal of (R)-3-[2-(2-hydroxymethylpyrrolidin-1-yl)ethyl]-5-methyl-2H-isoquinolin-1-one monosulfate having physicochemical properties shown by the following W and/or X:
W: having a powder X-ray diffraction pattern shown in FIG. 27,
X: having a thermogravimetry-differential thermal analysis curve shown in FIG. 28.

(76) (R)-3-[2-(2-Hydroxymethylpyrrolidin-1-yl)ethyl]-5-methyl-2H-isoquinolin-1-one monosulfate.

(77) The (R)-3-[2-(2-hydroxymethylpyrrolidin-1-yl)ethyl]-5-methyl-2H-isoquinolin-1-one monosulfate described above, which is a monohydrate.

(78) The (R)-3-[2-(2-hydroxymethylpyrrolidin-1-yl)ethyl]-5-methyl-2H-isoquinolin-1-one monosulfate described above, which is a crystal.

(79) A crystal of (R)-3-[2-(2-hydroxymethylpyrrolidin-1-yl)ethyl]-5-methyl-2H-isoquinolin-1-one monosulfate monohydrate.

(80) The crystal described above showing a powder X-ray diffraction spectrum having peaks at diffraction angles represented by 2θ of around 11.7°, 15.2° and 19.7° (each ±0.2°).

(81) A crystal of (R)-3-[2-(2-hydroxymethylpyrrolidin-1-yl)ethyl]-5-methyl-2H-isoquinolin-1-one monosulfate monohydrate having physicochemical properties shown by the following Y and/or Z:
Y: having a powder X-ray diffraction pattern shown in FIG. 29,
Z: having a thermogravimetry-differential thermal analysis curve shown in FIG. 30.

(82) (R)-3-[2-(2-Hydroxymethylpyrrolidin-1-yl)ethyl]-5-methyl-2H-isoquinolin-1-one mono-D-tartrate.

(83) The (R)-3-[2-(2-hydroxymethylpyrrolidin-1-yl)ethyl]-5-methyl-2H-isoquinolin-1-one mono-D-tartrate described above, which is a monohydrate.

(84) The (R)-3-[2-(2-hydroxymethylpyrrolidin-1-yl)ethyl]-5-methyl-2H-isoquinolin-1-one mono-D-tartrate described above, which is a crystal.

(85) A crystal of (R)-3-[2-(2-hydroxymethylpyrrolidin-1-yl)ethyl]-5-methyl-2H-isoquinolin-1-one mono-D-tartrate monohydrate.

(86) The crystal described above showing a powder X-ray diffraction spectrum having peaks at diffraction angles represented by 2θ of around 8.5°, 21.1° and 22.1° (each ±0.2°).

(87) The crystal described above having a melting point (extrapolated onset temperature) by thermogravimetry-differential thermal analysis of about 169° C.

(88) A crystal of (R)-3-[2-(2-hydroxymethylpyrrolidin-1-yl)ethyl]-5-methyl-2H-isoquinolin-1-one mono-D-tartrate monohydrate having physicochemical properties shown by the following a and/or b:
a: having a powder X-ray diffraction pattern shown in FIG. 31,
b: having a thermogravimetry-differential thermal analysis curve shown in FIG. 32.

(89) (R)-3-[2-(2-Hydroxymethylpyrrolidin-1-yl)ethyl]-5-methyl-2H-isoquinolin-1-one mono-L-tartrate.

(90) The (R)-3-[2-(2-hydroxymethylpyrrolidin-1-yl)ethyl]-5-methyl-2H-isoquinolin-1-one mono-L-tartrate described above, which is a monohydrate.

(91) The (R)-3-[2-(2-hydroxymethylpyrrolidin-1-yl)ethyl]-5-methyl-2H-isoquinolin-1-one mono-L-tartrate described above, which is a crystal.

(92) A crystal of (R)-3-[2-(2-hydroxymethylpyrrolidin-1-yl)ethyl]-5-methyl-2H-isoquinolin-1-one mono-L-tartrate monohydrate.

(93) The crystal described above showing a powder X-ray diffraction spectrum having peaks at diffraction angles represented by 2θ of around 7.2°, 16.2° and 22.0° (each ±0.2°).
(94) The crystal described above having a melting point (extrapolated onset temperature) by thermogravimetry-differential thermal analysis of about 148° C.
(95) A crystal of (R)-3-[2-(2-hydroxymethylpyrrolidin-1-yl)ethyl]-5-methyl-2H-isoquinolin-1-one mono-L-tartrate monohydrate having physicochemical properties shown by the following c and/or d:
c: having a powder X-ray diffraction pattern shown in FIG. 33,
d: having a thermogravimetry-differential thermal analysis curve shown in FIG. 34.
(96) A medicament comprising the compound described above.
(97) A pharmaceutical composition comprising the compound described above and a pharmaceutically acceptable additive.
(98) A poly(ADP-ribose)polymerase inhibitor comprising the compound described above as an active ingredient.
(99) A medicament for the prophylaxis and/or treatment of a disease caused by hyperactivity of a poly(ADP-ribose) polymerase, which comprises the compound described above as an active ingredient.
(100) A medicament for the prophylaxis and/or treatment of cerebral infarction, which comprises the compound described above as an active ingredient.
(101) A medicament for improving neurological symptoms associated with cerebral infarction, which comprises the compound described above as an active ingredient.
(102) The medicament described above, which is used in an acute stage of cerebral infarction.

Effect of the Invention

It is possible to provide a novel salt form of (R)-3-[2-(2-hydroxymethylpyrrolidin-1-yl)ethyl]-5-methyl-2H-isoquinolin-1-one.

BEST MODE FOR CARRYING OUT THE INVENTION

Figure 1:
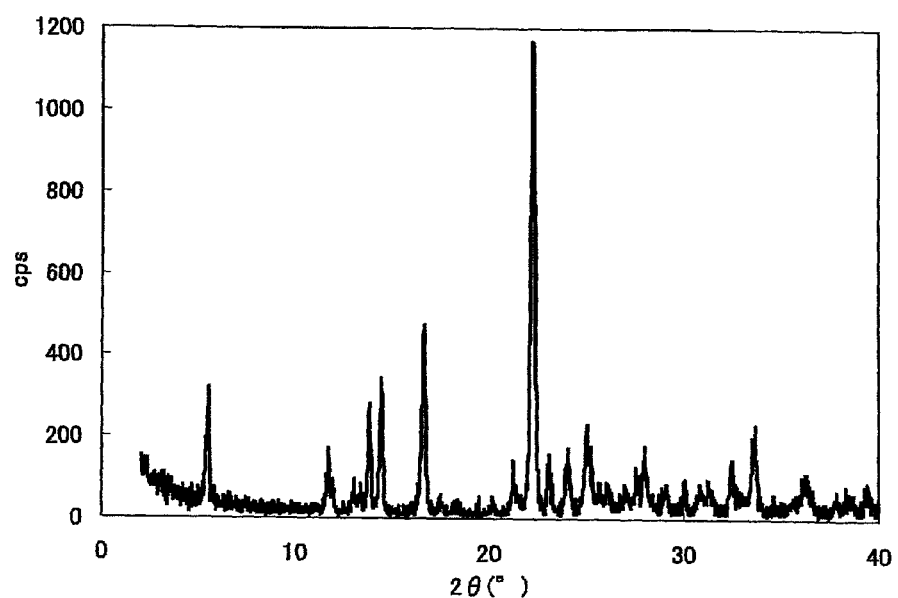
FIG. 1 shows a powder X-ray diffraction pattern of monohydrochloride dihydrate (form I crystal).

The present invention provides a novel salt form of (R)-3-[2-(2-hydroxymethylpyrrolidin-1-yl)ethyl]-5-methyl-2H-isoquinolin-1-one represented by the following compound (I):

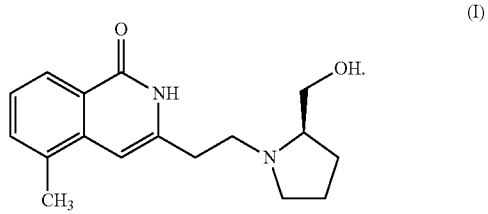

Compound (I) includes tautomers such as the following compound (II). In the present specification, compound names are indicated by the ketone form (compound (I)), which is considered to be generally stable, as a representative example of such tautomers. That is, while compound names are indicated using the ketone form in the present invention, exclusion of those present in an enol (compound (II)) form is not intended, and enol form compounds are also encompassed in the present invention.

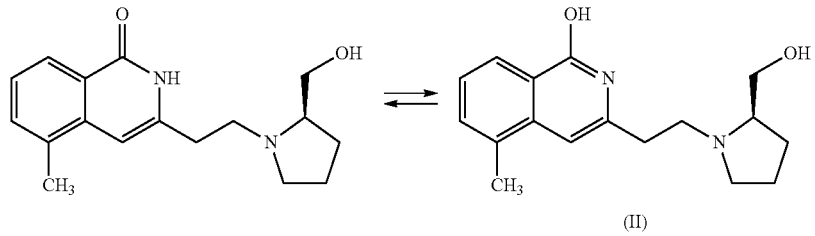

(II)

A preferable embodiment of monophosphate is anhydrate, and more preferable embodiment is crystal. Of the anhydrous monophosphate crystals, a crystal of a preferable embodiment has a powder X-ray diffraction pattern shown in FIG. 3 and/or a thermogravimetry-differential thermal analysis (hereinafter sometimes to be indicated as TG/DTA) curve shown in FIG. 4. Here, characteristic peaks in a powder X-ray diffraction spectrum are at diffraction angles represented by $2\theta$ of around 12.0°, 15.0°, 17.8°, 19.6°, 22.8° and/or 25.8° (each ±0.2°). In addition, the melting point (extrapolated onset temperature) by TG/DTA is about 216° C. to about 217° C., preferably about 216° C.

Monophosphate can be obtained by reacting, for example, more than 0.5 mol and less than 2 mol, preferably not less than 0.67 mol and not more than 1.1 mol, more preferably 1 mol of phosphoric acid per 1 mol of (R)-3-[2-(2-hydroxymethylpyrrolidin-1-yl)ethyl]-5-methyl-2H-isoquinolin-1-one (hereinafter sometimes to be indicated as a free form) that can be produced according to the synthesis method described in Example 36 of WO 2004/031171. In addition, it can also be obtained according to the methods of the Examples described later and the like.

In addition, monophosphate can also be obtained by using (R)-3-[2-(2-hydroxymethylpyrrolidin-1-yl)ethyl]-5-methyl-2H-isoquinolin-1-one hemiphosphate (hereinafter sometimes to be indicated simply as hemiphosphate), (R)-3-[2-(2-hydroxymethylpyrrolidin-1-yl)ethyl]-5-methyl-2H-isoquinolin-1-one diphosphate (hereinafter sometimes to be indicated simply as diphosphate) or anhydrous (R)-3-[2-(2-hydroxymethylpyrrolidin-1-yl)ethyl]-5-methyl-2H-iso-quinolin-1-one monohydrochloride (hereinafter sometimes to be indicated simply as anhydrous monohydrochloride) as a production intermediate or starting material.

Examples of the method for obtaining monophosphate from hemiphosphate include a method comprising reacting more than 0 mol and less than 1.5 mol, preferably not less than 0.17 mol and not more than 0.6 mol, more preferably 0.5 mol, of phosphoric acid per 1 mol of hemiphosphate. In addition, hemiphosphate can be converted to a free form and then to monophosphate, according to a method to be mentioned later comprising converting anhydrous monohydrochloride to a free form and then to monophosphate.

Examples of the method for obtaining monophosphate from diphosphate include reacting more than 0 mol and less than 3 mol, preferably not less than 0.8 mol and not more than 2 mol, more preferably 1 mol, of a free form per 1 mol of diphosphate. In addition, diphosphate can be converted to a free form and then to monophosphate, according to a method to be mentioned later comprising converting anhydrous monohydrochloride to a free form and then to monophosphate.

Examples of the method for obtaining monophosphate from anhydrous monohydrochloride, anhydrous monohydrobromide, monohydrobromide dihydrate, anhydrous monomesylate, anhydrous hemisulfate, hemisulfate sesquihydrate, anhydrous monosulfate, monosulfate monohydrate, mono-D-tartrate monohydrate or mono-L-tartrate monohydrate include adding anhydrous monohydrochloride to a biphasic solvent consisting of a suitable organic solvent such as dichloromethane, chloroform, ethyl acetate and the like and a suitable alkaline aqueous solution such as aqueous sodium hydroxide solution, aqueous potassium carbonate solution, aqueous sodium carbonate solution, aqueous sodium hydrogen carbonate solution and the like, shaking the mixture, obtaining a free form from an organic solvent layer, and reacting 1 mol of the obtained free form with more than 0.5 mol and less than 2 mol, preferably not less than 0.67 mol and not more than 1.1 mol, more preferably 1 mol, of phosphoric acid.

When obtaining monophosphate, a free form is once crudely purified as (R)-3-[2-(2-hydroxymethylpyrrolidin-1-yl)ethyl]-5-methyl-2H-isoquinolin-1-one monohydrochloride and then converted to monophosphate, whereby monophosphate with higher purity can be obtained.

Hemiphosphate can be obtained as a monohydrate crystal. Of the hemiphosphate monohydrate crystals, a crystal of a preferable embodiment has a powder X-ray diffraction pattern shown in FIG. 5 and/or a TG/DTA curve shown in FIG. 6. Here, characteristic peaks in a powder X-ray diffraction spectrum are at diffraction angles represented by $2\theta$ of around 8.8°, 11.8°, 14.4°, 21.4°, 23.7°, 24.6° and 26.6° (each ±0.2°). In addition, the melting point (extrapolated onset temperature) by TG/DTA is about 199° C. Hemiphosphate can be obtained according to a production method of monophosphate and using a free form as a starting material, or can also be obtained according to the methods of the Examples described later.

Diphosphate can be obtained as a crystal of monohydrate 0.5 ethanol solvate. Of the diphosphate monohydrate 0.5 ethanol solvate crystals, a crystal of a preferable embodiment has a powder X-ray diffraction pattern shown in FIG. 7 and/or a TG/DTA curve shown in FIG. 8. Here, characteristic peaks in a powder X-ray diffraction spectrum are at diffraction angles represented by $2\theta$ of around 6.6°, 13.1°, 23.1° and 26.4° (each ±0.2°). In addition, the melting point (extrapolated onset temperature) by TG/DTA is about 196° C. Diphosphate can be obtained according to a production method of monophosphate and using a free form as a starting material, and can also be obtained according to the methods of the Examples described later.

Anhydrous monohydrochloride can be obtained as a crystal. Of the anhydrous monohydrochloride crystals, a crystal of a preferable embodiment is a crystal (form II) having a powder X-ray diffraction pattern shown in FIG. 9 and/or a melting point (extrapolated onset temperature) by TG/DTA of about 110° C. Here, characteristic peaks in a powder X-ray diffraction spectrum are at diffraction angles represented by 2θ of around 6.7°, 21.8° and 30.2° (each ±0.2°). A crystal of another preferable embodiment is a crystal (form III) having a powder X-ray diffraction pattern shown in FIG. 10 and/or a melting point (extrapolated onset temperature) by TG/DTA of about 231° C. Here, characteristic peaks in a powder X-ray diffraction spectrum are at diffraction angles represented by 2θ of around 15.5°, 29.4°, 31.4°, 31.9° and 34.3° (each ±0.2°). A crystal of still another preferable embodiment is a crystal (form IV) having a powder X-ray diffraction pattern shown in FIG. 11 and/or a TG/DTA curve shown in FIG. 12. Here, characteristic peaks in a powder X-ray diffraction spectrum are at diffraction angles represented by 2θ of around 9.1°, 19.8°, 20.9° and 28.6° (each ±0.2°). In addition, the melting point (extrapolated onset temperature) by TG/DTA is about 208° C. Anhydrous monohydrochloride can be obtained by reacting 1 to 10 mol, preferably 1 to 2 mol, more preferably 1 mol, of hydrochloric acid per 1 mol of a free form. In addition, it can also be obtained according to the methods of the Examples described later.

Anhydrous monohydrobromide can be obtained as a crystal. Of the anhydrous monohydrobromide crystals, a crystal of a preferable embodiment is a crystal (form I) having a powder X-ray diffraction pattern shown in FIG. 15 and/or a melting point (extrapolated onset temperature) by TG/DTA of about 173° C. Here, characteristic peaks in a powder X-ray diffraction spectrum are at diffraction angles represented by 2θ of around 11.0°, 12.8° and 20.3° (each ±0.2°). A crystal of another preferable embodiment is a crystal (form II) having a powder X-ray diffraction pattern shown in FIG. 17 and/or a melting point (extrapolated onset temperature) by TG/DTA of about 235° C. Here, characteristic peaks in a powder X-ray diffraction spectrum are at diffraction angles represented by 2θ of around 8.3°, 9.2° and 14.0° (each ±0.2°). Anhydrous monohydrobromide can be obtained by reacting 1 to 10 mol, preferably 1 to 2 mol, more preferably 1 mol, of hydrobromic acid per 1 mol of a free form, and drying at low temperature to give form I crystal, or drying at a high temperature to give form II crystal. In addition, it can also be obtained according to the methods of the Examples described later.

Monohydrobromide dihydrate can be obtained as a crystal. Of the monohydrobromide dihydrate crystals, a crystal of a preferable embodiment is a crystal having a powder X-ray diffraction pattern shown in FIG. 19 and/or a TG/DTA curve shown in FIG. 20. Here, characteristic peaks in a powder X-ray diffraction spectrum are at diffraction angles represented by 2θ of around 11.7°, 17.4°, 21.1° and 26.0° (each ±0.2°). Monohydrobromide dihydrate can be obtained by reacting 1 to 10 mol, preferably 1 to 2 mol, more preferably 1 mol, of hydrobromic acid per 1 mol of a free form, and adjusting the humidity. In addition, it can also be obtained according to the methods of the Examples described later.

Anhydrous monomesylate can be obtained as a crystal. Of the anhydrous monomesylate crystals, a crystal of a preferable embodiment is a crystal having a powder X-ray diffraction pattern shown in FIG. 21 and/or a melting point (extrapolated onset temperature) by TG/DTA of about 176° C. Here, characteristic peaks in a powder X-ray diffraction spectrum are at diffraction angles represented by 2θ of around 15.6° and 20.7° (each ±0.2°). Anhydrous monomesylate can be obtained by reacting 1 to 10 mol, preferably 1 to 2 mol, more preferably 1 mol, of mesylic acid per 1 mol of a free form. In addition, it can also be obtained according to the methods of the Examples described later.

Anhydrous hemisulfate can be obtained as a crystal. Of the anhydrous hemisulfate crystals, a crystal of a preferable embodiment is a crystal having a powder X-ray diffraction pattern shown in FIG. 23 and/or a melting point (extrapolated onset temperature) by TG/DTA of about 166° C. Here, characteristic peaks in a powder X-ray diffraction spectrum are at diffraction angles represented by 2θ of around 7.2°, 13.1° and 25.2° (each ±0.2°). Anhydrous hemisulfate can be obtained by reacting 0.3 to 0.6 mol, preferably 0.5 mol, of sulfuric acid per 1 mol of a free form. In addition, it can also be obtained according to the methods of the Examples described later.

Hemisulfate sesquihydrate can be obtained as a crystal. Of the hemisulfate sesquihydrate crystals, a crystal of a preferable embodiment is a crystal having a powder X-ray diffraction pattern shown in FIG. 25 and/or a melting point (extrapolated onset temperature) by TG/DTA of about 106° C. Here, characteristic peaks in a powder X-ray diffraction spectrum are at diffraction angles represented by 2θ of around 5.3°, 8.1°, 10.6° and 22.9° (each ±0.2°). Hemisulfate sesquihydrate can be obtained by reacting 0.3 to 0.6 mol, preferably 0.5 mol, of sulfuric acid per 1 mol of a free form, and adjusting the humidity. In addition, it can also be obtained according to the methods of the Examples described later.

Anhydrous monosulfate can be obtained as a crystal. Of the anhydrous monosulfate crystals, a crystal of a preferable embodiment is a crystal having a powder X-ray diffraction pattern shown in FIG. 27 and/or a melting point (extrapolated onset temperature) by TG/DTA of about 176° C. Here, characteristic peaks in a powder X-ray diffraction spectrum are at diffraction angles represented by 2θ of around 12.2° and 21.7° (each ±0.2°). Anhydrous monosulfate can be obtained by reacting 1 to 10 mol, preferably 1 to 2 mol, more preferably 1 mol, of sulfuric acid per 1 mol of a free form. In addition, it can also be obtained according to the methods of the Examples described later.

Monosulfate monohydrate can be obtained as a crystal. Of the monosulfate monohydrate crystals, a crystal of a preferable embodiment is a crystal having a powder X-ray diffraction pattern shown in FIG. 29 and/or a TG/DTA curve shown in FIG. 30. Here, characteristic peaks in a powder X-ray diffraction spectrum are at diffraction angles represented by 2θ of around 11.7°, 15.2° and 19.7° (each ±0.2°). Monosulfate monohydrate can be obtained by reacting 1 to 10 mol, preferably 1 to 2 mol, more preferably 1 mol, of sulfuric acid per 1 mol of a free form, and adjusting the humidity. In addition, it can also be obtained according to the methods of the Examples described later.

Mono-D-tartrate monohydrate can be obtained as a crystal. Of the mono-D-tartrate monohydrate crystals, a crystal of a preferable embodiment is a crystal having a powder X-ray diffraction pattern shown in FIG. 31 and/or a melting point (extrapolated onset temperature) by TG/DTA of about 169° C. Here, characteristic peaks in a powder X-ray diffraction spectrum are at diffraction angles represented by 2θ of around 8.5°, 21.1° and 22.1° (each ±0.2°). Mono-D-tartrate monohydrate can be obtained by reacting 1 to 10 mol, preferably 1 to 2 mol, more preferably 1 mol, of D-tartaric acid per 1 mol of a free form. In addition, it can also be obtained according to the methods of the Examples described later.

Mono-L-tartrate monohydrate can be obtained as a crystal. Of the mono-L-tartrate monohydrate crystals, a crystal of a preferable embodiment is a crystal having a powder X-ray diffraction pattern shown in FIG. 33 and/or a melting point (extrapolated onset temperature) by TG/DTA of about 148° C. Here, characteristic peaks in a powder X-ray diffraction spectrum are at diffraction angles represented by 2θ of around 7.2°, 16.2° and 22.0° (each ±0.2°). Mono-L-tartrate monohydrate can be obtained by reacting 1 to 10 mol, preferably 1 to 2 mol, more preferably 1 mol, of L-tartaric acid per 1 mol of a free form. In addition, it can also be obtained according to the methods of the Examples described later.

Monophosphate is present as (R)-3-[2-(2-hydroxymethylpyrrolidin-1-yl)ethyl]-5-methyl-2H-isoquinolin-1-one in a solution state, and it is known that this compound possesses a potent PARP inhibitory action (WO 2004/031171, Experimental Example, Table 1 (pp. 82-83)). Thus, monophosphate is useful as a PARP inhibitor, and useful as a drug for the prophylaxis and/or treatment of cerebral infarction (more preferably in acute stage of cerebral infarction) or improvement of neurological symptoms associated with cerebral infarction (more preferably in acute stage of cerebral infarction).

When monophosphate is used as the aforementioned prophylactic and/or therapeutic drug, it can be generally administered orally or parenterally in the form of a pharmaceutical composition or preparation (e.g., tablet, liquid etc.) obtained by mixing monophosphate with a pharmaceutically acceptable carrier. The pharmaceutical composition can be formulated into a preparation according to a conventional method.

The dose is determined according to the age, body weight, general health condition, sex, diet, administration time, administration method, clearance rate, combination of drugs, and the level of disease for which patients are undergoing treatments at that time, or further in consideration of other factors. Monophosphate is low toxic and can be used safely. While the daily dose thereof varies depending on the condition and body weight of patient, the kind of the compound, administration route and the like, it is preferably, for example, 0.01 to 150 mg/patient/day by oral administration, and about 0.01 to 50 mg/patient/day by parenteral administration.

In the present specification, the "prophylactic drug" is a drug to be administered to a healthy person who has not developed a disease and is, for example, a drug to be administered for the purpose of preventing the onset of a disease. The "therapeutic drug" is a drug to be administered by a doctor to a person diagnosed by a doctor to have developed a disease (patient) and is, for example, a drug to be administered for the purpose of alleviating a disease or symptom, or recovering health. Even when the object of administration is prevention of aggravation of a disease or symptom, or prevention of attack, as long as it is administered to a patient, it is a therapeutic drug.

EXAMPLES

The present invention is explained in detail in the following by referring to Examples and the like, which are not to be construed as limitative.

The chemical shift value of $^1$H-NMR was measured using tetramethylsilane (TMS) as an internal standard and the relative delta (δ) value is shown in parts per million (ppm). As for the coupling constant, obvious multiplicity is shown in hertz (Hz), using s (singlet), d (doublet), t (triplet), q (quartet), sept (septet), m (multiplet), dd (double doublet), brs (broad singlet) and the like.

Production Example 1

(R)-3-[2-(2-hydroxymethylpyrrolidin-1-yl)ethyl]-5-methyl-2H-isoquinolin-1-one monohydrochloride dihydrate (Form I Crystal; Hereinafter Sometimes to be Indicated Simply as Monohydrochloride Dihydrate)

Figure 2:
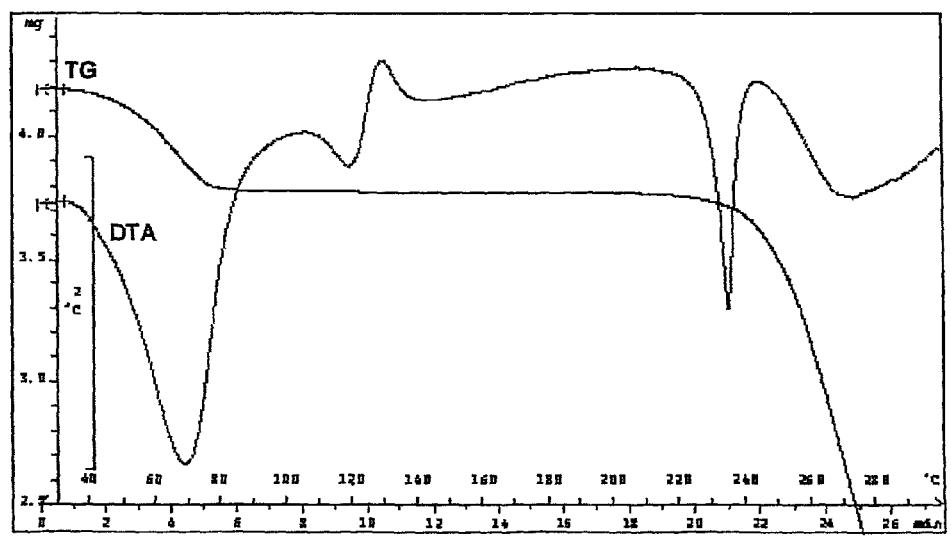
FIG. 2 shows a TG/DTA curve of monohydrochloride dihydrate (form I crystal).

To a solution of a free form obtained according to the method described in WO 2004/031171 was added hydrochloric acid and the mixture was stirred to give (R)-3-[2-(2-hydroxymethylpyrrolidin-1-yl)ethyl]-5-methyl-2H-isoquinolin-1-one monohydrochloride. The obtained compound was humidity-conditioned for 7 days in a desiccator with 75% of relative humidity (sodium chloride humidity-conditioned salt) to give the title compound.

elemental analysis
$C_{17}H_{22}N_2O_2 \cdot 1HCl \cdot 2H_2O$
Calculated; C: 56.90, H: 7.58, N: 7.81, Cl: 9.88
Found; C: 56.98, H: 7.33, N: 7.57, Cl: 9.74
measurement method and results of powder X ray apparatus: RINT2200/Ultima+ (Rigaku Corporation)
X-ray: Cu K-ALPHA/40 kV/40 mA
goniometer: Ultima+horizon goniometer TYPE I
attachment: standard sample holder
filter: not used
counter monochromator: fixed monochromator
divergence slit: 0.5°/scattering slit: 0.73 mm/receiving slit: 0.3 mm
scanning mode: continuous
scan speed: 4°/min
sampling period: 0.02°
scan axis: 2θ/θ
scan range: 2-40°
cumulated number: 1
measurement operation: A powder sample was filled in a flat plate sample holder (nonreflecting sample plate; Si single crystal) and adjusted by forming a smooth surface to give a measurement sample. The sample holder was correctly set at a predetermined position of a powder X-ray diffraction apparatus, and the powder X-ray diffraction pattern was measured. The powder X-ray diffraction pattern of the compound is shown in FIG. 1. The characteristic peaks of the crystal were at diffraction angles represented by 2θ of 11.7°, 23.1°, 28.0° and 33.6° (±0.2°).
measurement method and results of melting point (TG/DTA) apparatus: TG/SDTA 851e (Mettler-Toledo Inc.)
measurement condition: measurement range 25° C.-300° C.
temperature rise rate 10 K/min
atmospheric nitrogen 40 mL/min
measurement operation: A sample (4.2 mg) was filled in a sample container (aluminum, 40 μL, with lid and foraminula). This was correctly set at a predetermined position in the apparatus, and weight changes (TG) of the sample during temperature rise process and temperature difference (DTA) from that of the standard substance were measured, while heating the container according to a predetermined temperature program. The results are shown in FIG. 2.

Example 1 anhydrous (R)-3-[2-(2-hydroxymethylpyrrolidin-1-yl)ethyl]-5-methyl-2H-isoquinolin-1-one monophosphate A free form (1 g) of (R)-3-[2-(2-hydroxymethylpyrrolidin-1-yl)ethyl]-5-methyl-2H-isoquinolin-1-one was measured, ethanol (40 ml) was added and the mixture was completely dissolved by heating under reflux. Thereto was added commercially available 85% phosphoric acid (200 μL) and the mixture was left stirring at room temperature for 1 hr. The precipitate was collected by filtration and dissolved again in water (1 mL) at 80° C. Ethanol (8 mL) was added and the mixture was left standing at room temperature for 1 hr. The resulting precipitate was collected by filtration and dried under reduced pressure at 50° C. for 9 hr to give the title compound (838 mg).

¹H-NMR

δ: 1.56-1.94 (4H, m), 2.46 (3H, s), 2.50-2.87 (5H, m), 3.22-3.54 (4H, m), 6.47 (1H, s), 7.30 (1H, t, J=8 Hz), 7.50 (1H, d, J=7 Hz), 8.00 (1H, d, J=8 Hz)

elemental analysis $C_{17}H_{22}N_2O_2 \cdot 1H_3O_4P$

Calculated; C: 53.12, H: 6.56, N: 7.29, P: 8.06

Found; C: 52.87, H: 6.63, N: 7.27, P: 7.87 measurement method and results of powder X-ray

Figure 3:
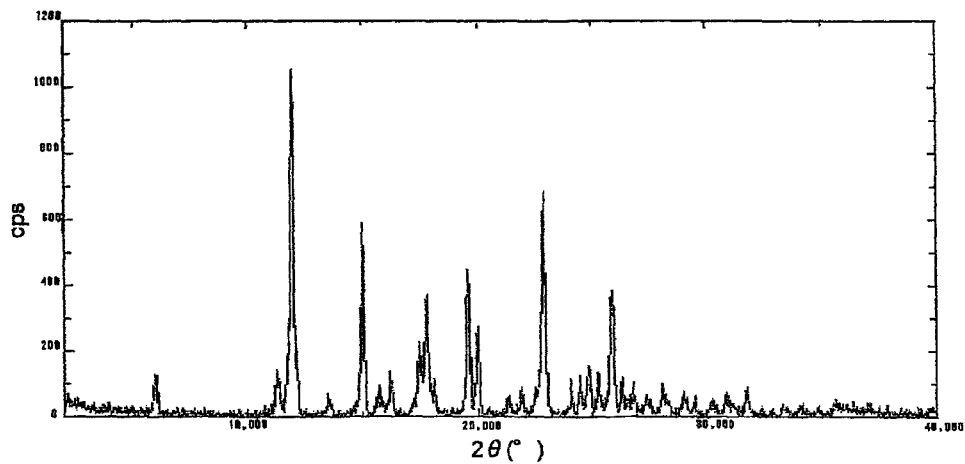
FIG. 3 shows a powder X-ray diffraction pattern of anhydrous monophosphate.

By a method similar to that of Production Example 1, powder X-ray diffraction pattern was measured. The results are shown in FIG. 3. The characteristic peaks of the crystal were at diffraction angles represented by 2θ of 12.0°, 15.0°, 17.8°, 19.6°, 20.0°, 22.8° and 25.8° (±0.2°).

measurement method and results of melting point (TG/DTA)

Figure 4:
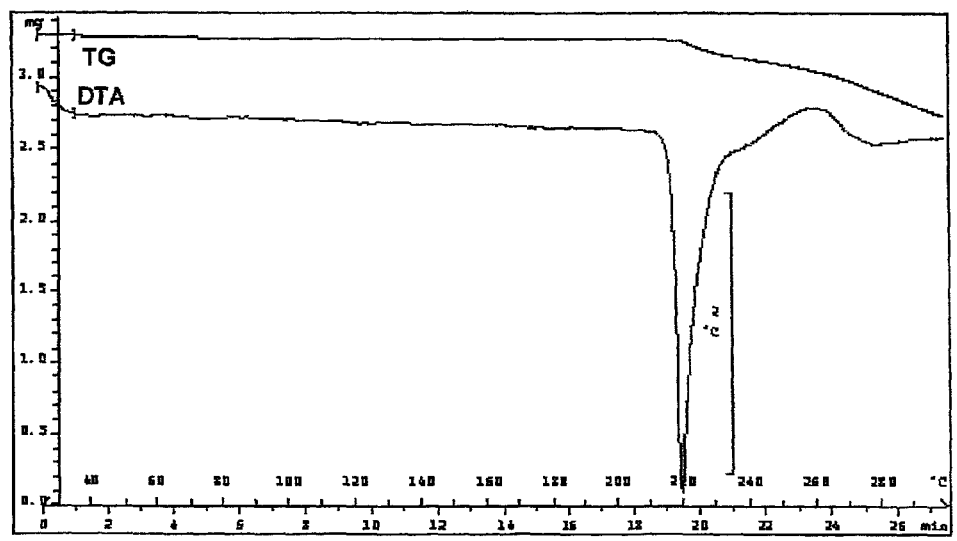
FIG. 4 shows a TG/DTA curve of anhydrous monophosphate.

By a method similar to that of Production Example 1, weight changes (TG) of the sample and temperature difference (DTA) from that of the standard substance were measured. The results are shown in FIG. 4. The melting point (extrapolated onset temperature) was 216° C.

Example 2

(R)-3-[2-(2-hydroxymethylpyrrolidin-1-yl)ethyl]-5-methyl-2H-isoquinolin-1-one hemiphosphate monohydrate A free form (502 mg) of (R)-3-[2-(2-hydroxymethylpyrrolidin-1-yl)ethyl]-5-methyl-2H-isoquinolin-1-one was measured in a reaction test tube, aqueous ethanol (5.8 mL, ethanol:water=8:1) was added and the mixture was completely dissolved by heating under reflux. Thereto was added aqueous phosphoric acid solution (501 μL, solution prepared by diluting commercially available 85% phosphoric acid (2.02 g) with the above-mentioned aqueous ethanol to scale up to 10 mL), and the mixture was stirred at room temperature for one day and left standing. The precipitate was collected by filtration. The precipitate (301 mg) was measured in a reaction test tube, and aqueous ethanol (2.6 mL, ethanol:water=4:1) was added. The mixture was completely dissolved by heating under reflux, stirred at room temperature for one day and left standing. The precipitate was collected by filtration, and dried under reduced pressure at 50° C. for 5 hr to give the title compound (264 mg).

elemental analysis $C_{17}H_{22}N_2O_2 \cdot 0.5H_3O_4P \cdot 1H_2O$

Calculated; C: 57.78, H: 7.27, N: 7.93, P: 4.38

Found; C: 57.80, H: 7.30, N: 7.84, P: 4.08 measurement method and results of powder X-ray

Figure 5:
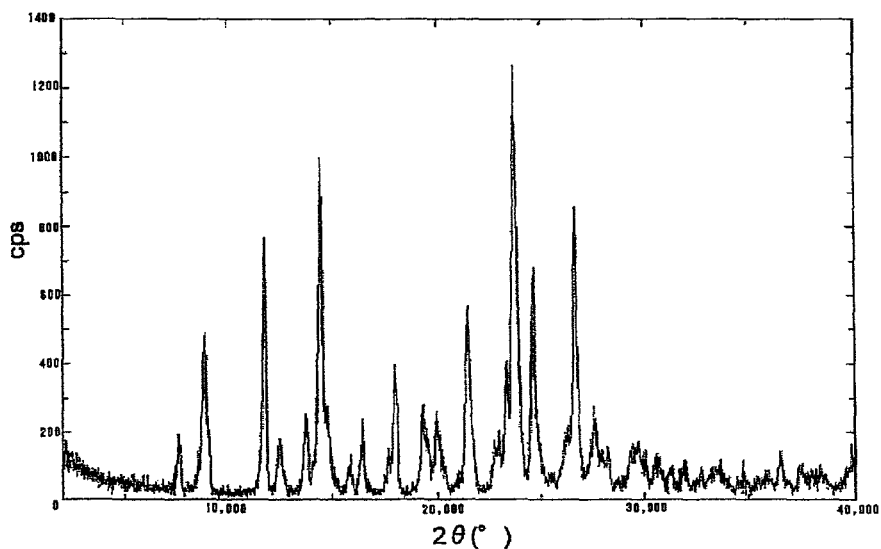
FIG. 5 shows a powder X-ray diffraction pattern of hemiphosphate monohydrate.

By a method similar to that of Production Example 1, powder X-ray diffraction pattern was measured. The results are shown in FIG. 5. The characteristic peaks of the crystal were at diffraction angles represented by 2θ of 8.8°, 11.8°, 14.4°, 21.4°, 23.7°, 24.6° and 26.6° (±0.2°).

measurement method and results of melting point (TG/DTA)

Figure 6:
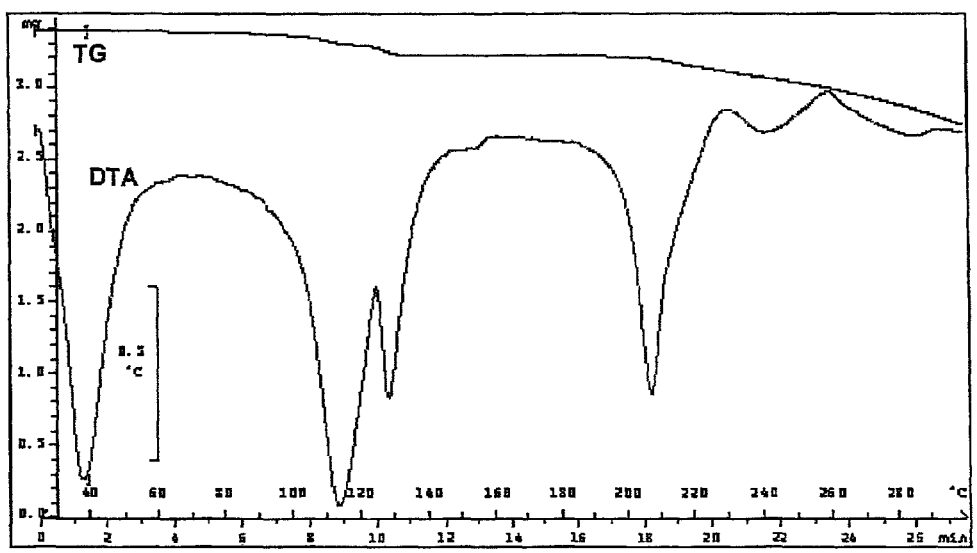
FIG. 6 shows a TG/DTA curve of hemiphosphate monohydrate.

By a method similar to that of Production Example 1, weight changes (TG) of the sample and temperature difference (DTA) from that of the standard substance were measured. The results are shown in FIG. 6. The melting point (extrapolated onset temperature) was 199° C.

Example 3

(R)-3-[2-(2-hydroxymethylpyrrolidin-1-yl)ethyl]-5-methyl-2H-isoquinolin-1-one diphosphate monohydrate 0.5 ethanol solvate A free form (501 mg) of (R)-3-[2-(2-hydroxymethylpyrrolidin-1-yl)ethyl]-5-methyl-2H-isoquinolin-1-one was measured in a reaction test tube, aqueous ethanol (4.3 mL, ethanol:water=8:1) was added and the mixture was completely dissolved by heating under reflux. Thereto was added aqueous phosphoric acid solution (2 mL, solution prepared by diluting commercially available 85% phosphoric acid (2.02 g) with the above-mentioned aqueous ethanol to scale up to 10 mL), and the mixture was stirred at room temperature for one day and left standing. The precipitate was collected by filtration. The obtained precipitate (302 mg) was measured in a reaction test tube, aqueous ethanol (2.4 mL, ethanol:water=6:1) was added, and the mixture was completely dissolved by heating under reflux. The mixture was stirred at room temperature for one day and left standing. The precipitate was collected by filtration and dried under reduced pressure at 50° C. for 5 hr to give the title compound (260 mg).

elemental analysis $C_{17}H_{22}N_2O_2 \cdot 2H_3O_4P \cdot 1H_2O \cdot 0.5C_2H_6O$ Calculated; C: 41.36, H: 6.28, N: 5.41, P: 11.97

Found; C: 41.30, H: 6.35, N: 5.35, P: 11.84 measurement method and results of powder X-ray

Figure 7:
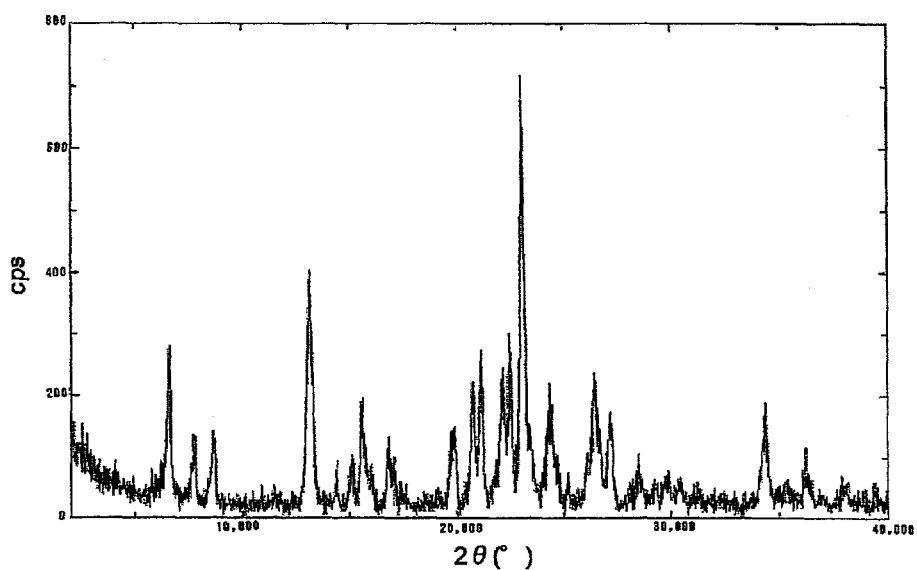
FIG. 7 shows a powder X-ray diffraction pattern of diphosphate monohydrate 0.5 ethanol solvate.

By a method similar to that of Production Example 1, powder X-ray diffraction pattern was measured. The results are shown in FIG. 7. The characteristic peaks of the crystal were at diffraction angles represented by 2θ of 6.6°, 13.1°, 23.1° and 26.4° (±0.2°).

measurement method and results of melting point (TG/DTA)

Figure 8:
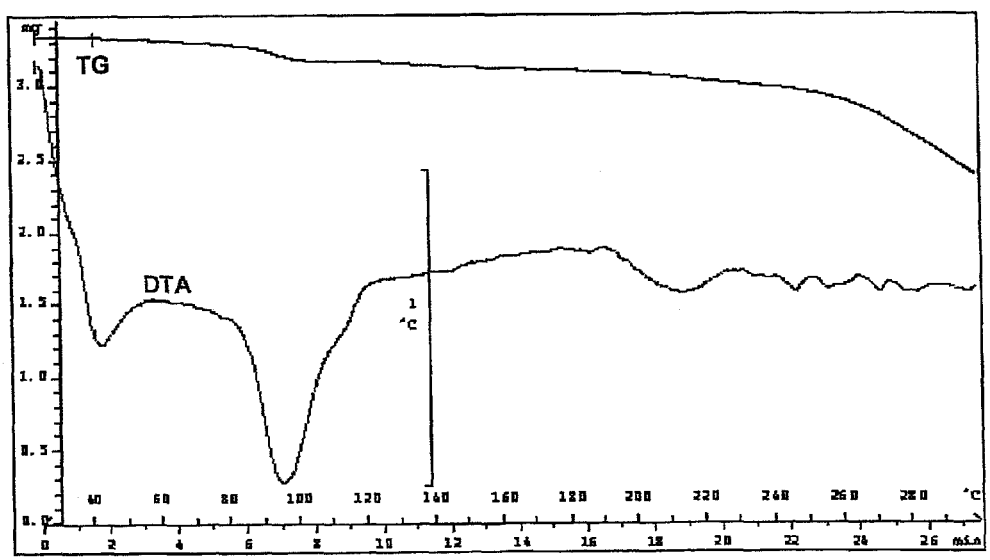
FIG. 8 shows a TG/DTA curve of diphosphate monohydrate 0.5 ethanol solvate.

By a method similar to that of Production Example 1, weight changes (TG) of the sample and temperature difference (DTA) from that of the standard substance were measured. The results are shown in FIG. 8. The melting point (extrapolated onset temperature) was 196° C.

Example 4 anhydrous (R)-3-[2-(2-hydroxymethylpyrrolidin-1-yl)ethyl]-5-methyl-2H-isoquinolin-1-one monohydrochloride (form II crystal)

Monohydrochloride dihydrate crystal (6.9 mg) was dried at 30° C., 5% of relative humidity or below for 7 hr to give the title compound (form II crystal) as crystals almost quantitatively.

measurement method and results of powder X-ray

Figure 9:
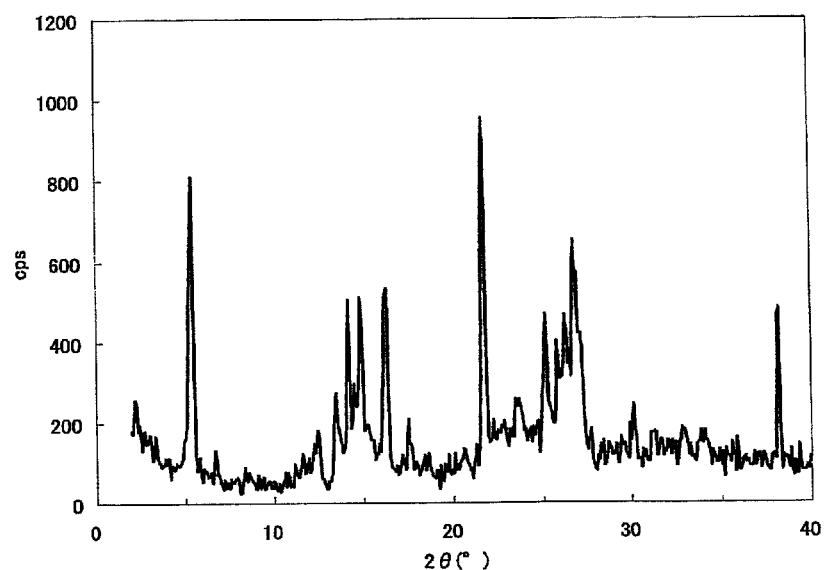
FIG. 9 shows a powder X-ray diffraction pattern of anhydrous monohydrochloride (form II crystal).

By a method similar to that of Production Example 1, powder X-ray diffraction pattern was measured. The results are shown in FIG. 9. The characteristic peaks of the crystal were at diffraction angles represented by 2θ of 6.7°, 21.8° and 30.2° (±0.2°).

The melting point (extrapolated onset temperature) from FIG. 2 was 110° C.

Example 5 anhydrous (R)-3-[2-(2-hydroxymethylpyrrolidin-1-yl)ethyl]-5-methyl-2H-isoquinolin-1-one monohydrochloride (form III crystal)

The compound (6 mg) obtained in Example 4 was heated to 200° C. at 5% of relative humidity or below to give the title compound (form III crystal) as crystals almost quantitatively.

measurement method and results of powder X-ray

Figure 10:
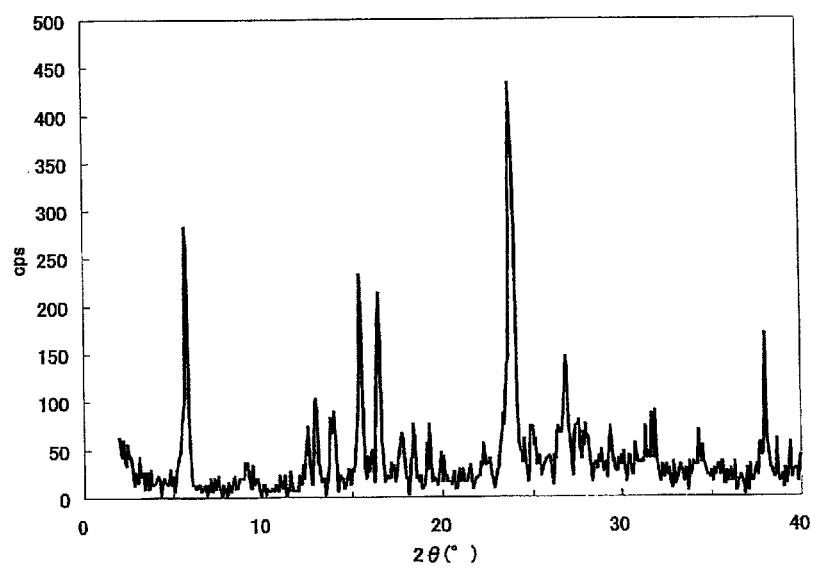
FIG. 10 shows a powder X-ray diffraction pattern of anhydrous monohydrochloride (form III crystal).

By a method similar to that of Production Example 1, powder X-ray diffraction pattern was measured. The results are shown in FIG. 10. The characteristic peaks of the crystal were at diffraction angles represented by 2θ of 15.5°, 29.4°, 31.4°, 31.9° and 34.3° (±0.2°).

The melting point (extrapolated onset temperature) from FIG. 2 was 231° C.

Example 6 anhydrous (R)-3-[2-(2-hydroxymethylpyrrolidin-1-yl)ethyl]-5-methyl-2H-isoquinolin-1-one monohydrochloride (form IV crystal)

(R)-3-[2-(2-Hydroxymethylpyrrolidin-1-yl)ethyl]-5-methyl-2H-isoquinolin-1-one monohydrochloride (4.65 g) was dissolved in ethanol/water mixed solvent while stirring with heating, and the mixture was cooled to room temperature. The resulting precipitate was collected by filtration, washed with ethyl acetate and dried under reduced pressure at 80° C. to give the title compound (2.3 g, form IV crystal).

elemental analysis $C_{17}H_{22}N_2O_2 \cdot 1HCl \cdot 0.54H_2O$ (as a result of the TG/DTA measurement to be mentioned later, weight decrease was observed from around room temperature, and therefore, 0.54 $H_2O$ is not crystal water but considered to be attached water, whereby the title compound is considered to be anhydrate)

Calculated; C: 61.40, H: 7.30, N: 8.42

Found; C: 61.10, H: 7.07, N: 8.25 measurement method and results of powder X-ray

Figure 11:
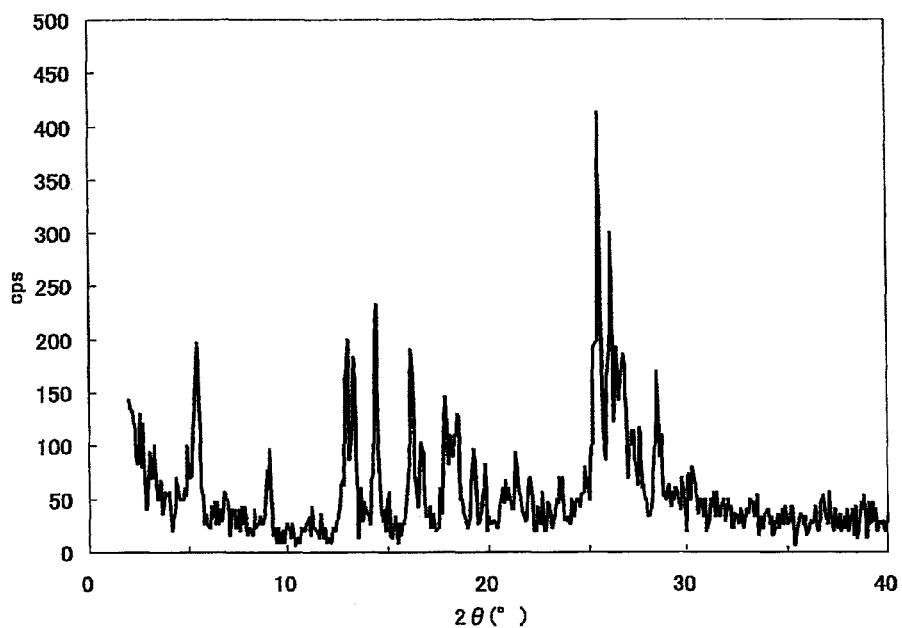
FIG. 11 shows a powder X-ray diffraction pattern of anhydrous monohydrochloride (form IV crystal).

By a method similar to that of Production Example 1, powder X-ray diffraction pattern was measured. The results are shown in FIG. 11. The characteristic peaks of the crystal were at diffraction angles represented by 2θ of 9.1°, 19.8°, 20.9°, 28.6° and 28.8° (±0.2°).

measurement method and results of melting point (TG/DTA)

Figure 12:
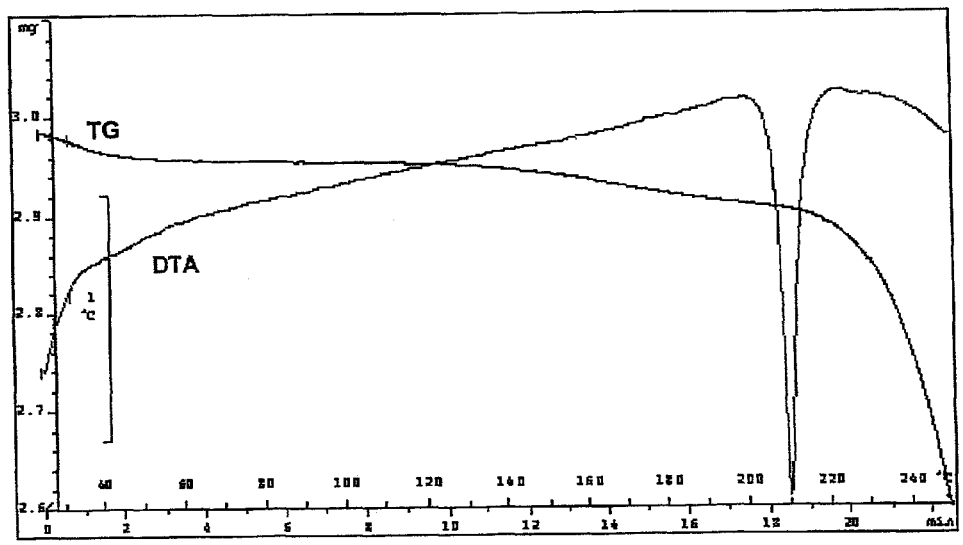
FIG. 12 shows a TG/DTA curve of anhydrous monohydrochloride (form IV crystal).

By a method similar to that of Production Example 1 except that the measurement range was changed to 25° C.-250° C., weight changes (TG) of the sample and temperature difference (DTA) from that of the standard substance were measured. The results are shown in FIG. 12. The melting point (extrapolated onset temperature) was 208° C. Also, from the behavior of moisture weight decrease, the compound was confirmed to be anhydrate.

Example 7 anhydrous (R)-3-[2-(2-hydroxymethylpyrrolidin-1-yl)ethyl]-5-methyl-2H-isoquinolin-1-one monohydrobromide (form I crystal)

To a solution (12 mL) of a free form (750 mg) of (R)-3-[2-(2-hydroxymethylpyrrolidin-1-yl)ethyl]-5-methyl-2H-isoquinolin-1-one in ethanol was added dropwise 2M HBr ethanol solution (1.5 mL) with stirring on an oil bath at 50° C. The bath was removed, seed crystals were added and the mixture was stirred to allow precipitation of crystals. After stirring for 1 hr at room temperature followed by under ice-cooling for 30 min, the crystals were collected through filtration, washed with ethanol and dried to give 885 mg of salt. Water (2 mL) was added to the salt, and the mixture was stirred to'dissolve completely under heating. In the same manner as above, the bath was removed and seed crystals were added. After stirring at room temperature followed by under ice-cooling, the crystals were collected through filtration, and washed with cold water. The crystals were dried under reduced pressure at 50° C. for 18 hr to give the title compound (707 mg).

$^1$H-NMR

δ:1.74-2.13 (4H, m), 2.49 (3H, s), 2.95-3.43 (4H, m), 3.56-3.81 (5H, m), 5.51 (1H, t, J=5 Hz), 6.55 (1H, s), 7.34 (1H, t, J=8 Hz), 7.54 (1H, d, J=7 Hz), 8.02 (1H, d, J=8 Hz), 9.24 (1H, brs), 11.43 (1H, brs)

elemental analysis $C_{17}H_{22}N_2O_2 \cdot 1HBr \cdot 0.5H_2O$ (as a result of the TG/DTA measurement to be mentioned later, weight decrease was observed from around room temperature, and therefore, 0.54 $H_2O$ is not crystal water but considered to be attached water, whereby the title compound is considered to be anhydrate)

Calculated; C: 54.26, H: 6.43, N: 7.44, Br: 21.20

Found; C: 54.50, H: 6.24, N: 7.38, Br: 21.07 measurement method and results of powder X-ray

Figure 15:
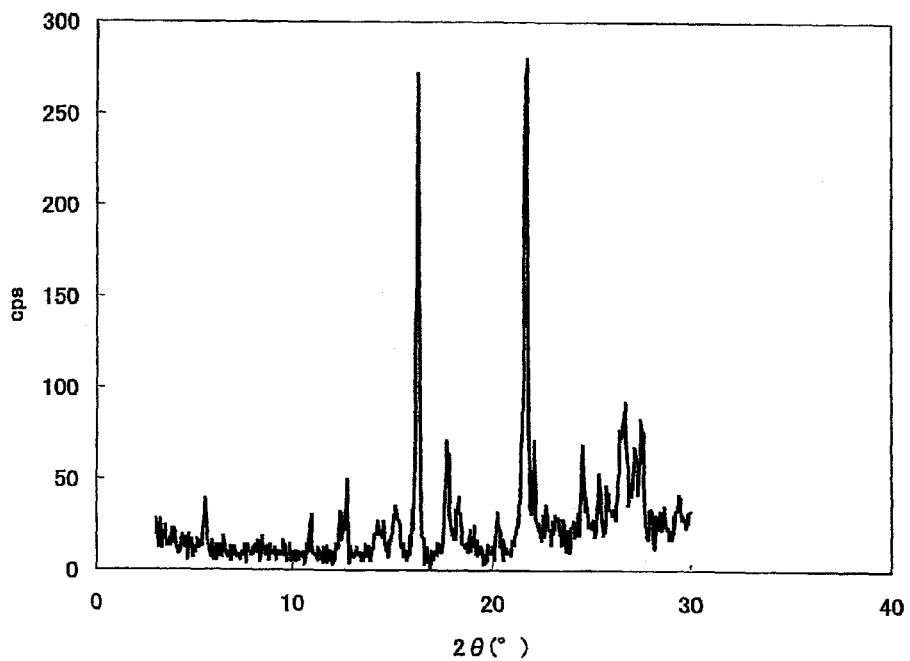
FIG. 15 shows a powder X-ray diffraction pattern of anhydrous monohydrobromide (form I crystal).

By a method similar to that of Production Example 1, powder X-ray diffraction pattern was measured. The results are shown in FIG. 15. The characteristic peaks of the crystal were at diffraction angles represented by 2θ of 11.0°, 12.8° and 20.3° (±0.2°).

measurement method and results of melting point (TG/DTA)

Figure 16:
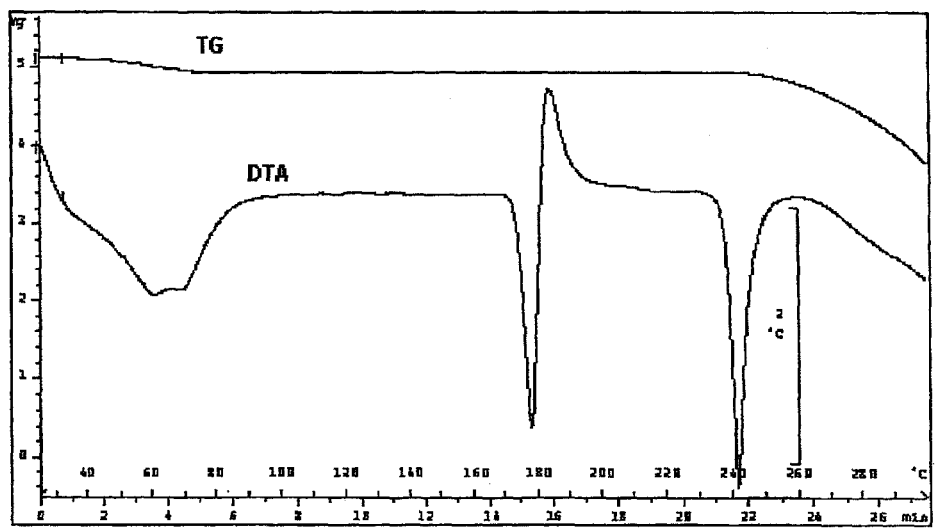
FIG. 16 shows a TG/DTA curve of anhydrous monohydrobromide (form I crystal).

By a method similar to that of Production Example 1, weight changes (TG) of the sample and temperature difference (DTA) from that of the standard substance were measured. The results are shown in FIG. 16. The melting point (extrapolated onset temperature) was 173° C.

Example 8 anhydrous (R)-3-[2-(2-hydroxymethylpyrrolidin-1-yl)ethyl]-5-methyl-2H-isoquinolin-1-one monohydrobromide (form II crystal)

(R)-3-[2-(2-Hydroxymethylpyrrolidin-1-yl)ethyl]-5-methyl-2H-isoquinolin-1-one anhydrous monohydrobromide (form I crystal) was heated under normal pressure at 190° C. for 4 hr to give the title compound.

measurement method and results of powder X-ray

Figure 17:
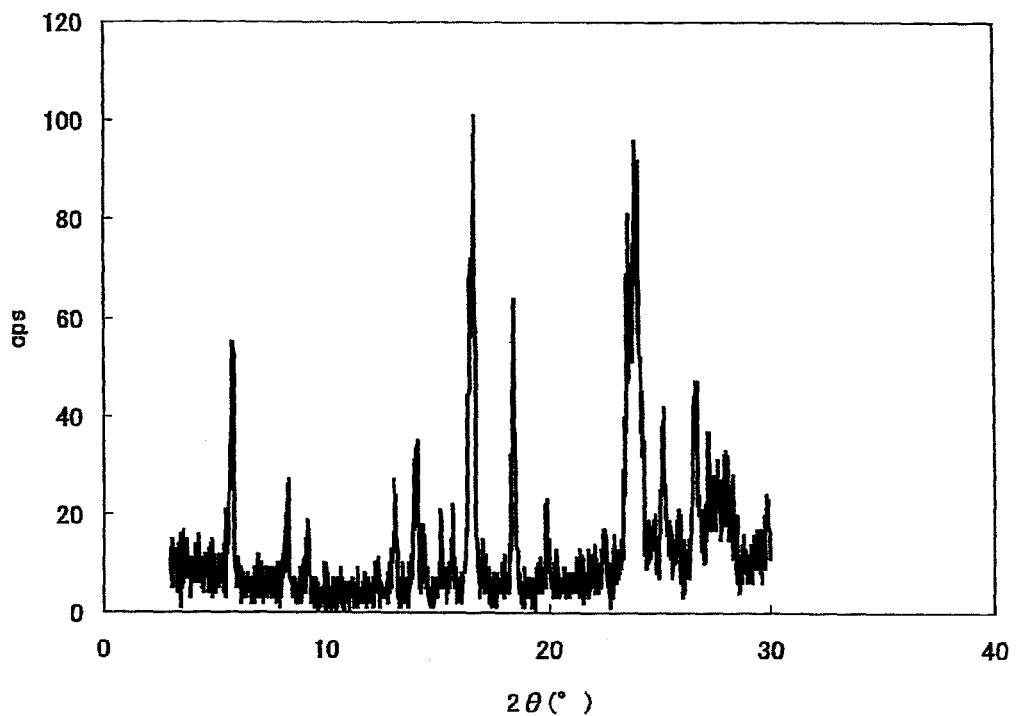
FIG. 17 shows a powder X-ray diffraction pattern of anhydrous monohydrobromide (form II crystal).

By a method similar to that of Production Example 1, powder X-ray diffraction pattern was measured. The results are shown in FIG. 17. The characteristic peaks of the crystal were at diffraction angles represented by 2θ of 8.3°, 9.2° and 14.0° (±0.2°).

measurement method and results of melting point (TG/DTA)

Figure 18:
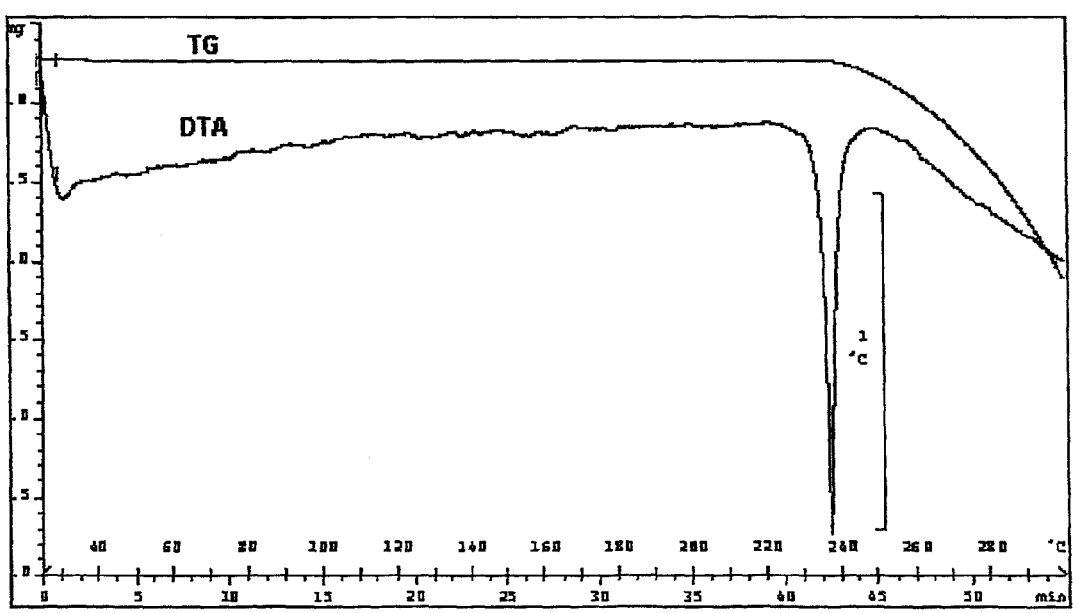
FIG. 18 shows a TG/DTA curve of anhydrous monohydrobromide (form II crystal).

By a method similar to that of Production Example 1, weight changes (TG) of the sample and temperature difference (DTA) from that of the standard substance were measured. The results are shown in FIG. 18. The melting point (extrapolated onset temperature) was 235° C.

Example 9

(R)-3-[2-(2-hydroxymethylpyrrolidin-1-yl)ethyl]-5-methyl-2H-isoquinolin-1-one monohydrobromide dihydrate (R)-3-[2-(2-Hydroxymethylpyrrolidin-1-yl)ethyl]-5-methyl-2H-isoquinolin-1-one anhydrous monohydrobromide (form I crystal) was preserved in a desiccator at room temperature, 75% of relative humidity for 6 days to give the title compound.

elemental analysis $C_{17}H_{22}N_2O_2 \cdot 1HBr \cdot 2H_2O$

Calculated; C: 50.63, H: 6.75, N: 6.95

Found; C: 50.73, H: 6.68, N: 6.86 measurement method and results of powder X-ray

Figure 19:
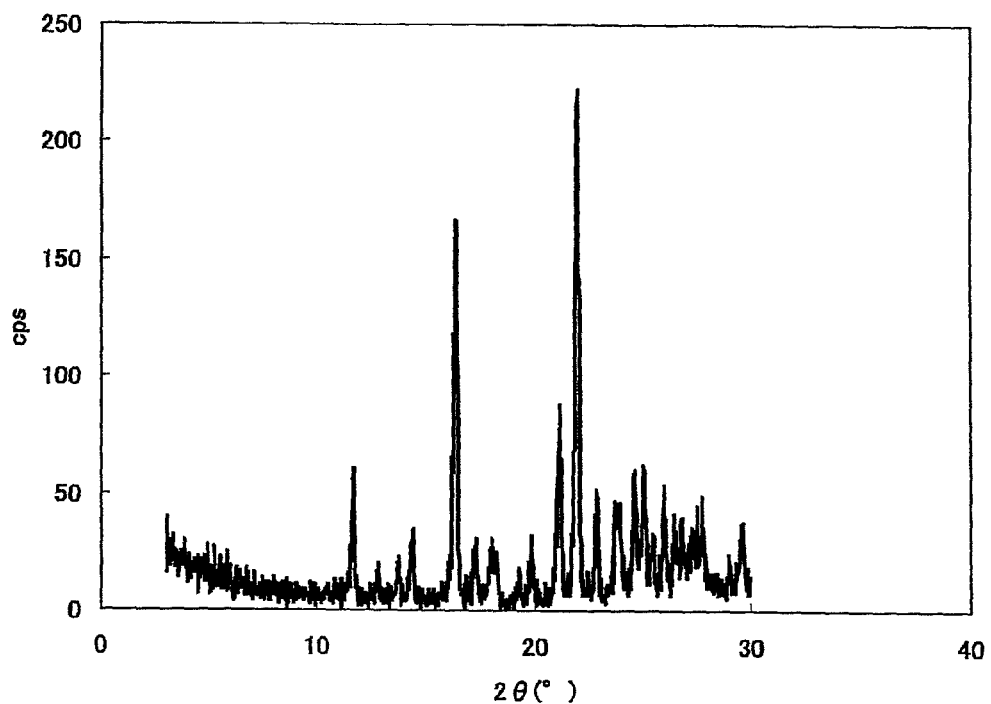
FIG. 19 shows a powder X-ray diffraction pattern of monohydrobromide dihydrate.

By a method similar to that of Production Example 1, powder X-ray diffraction pattern was measured. The results are shown in FIG. 19. The characteristic peaks of the crystal were at diffraction angles represented by 2θ of 11.7°, 17.4°, 21.1° and 26.0° (±0.2°).

measurement method and results of melting point (TG/DTA)

Figure 20:
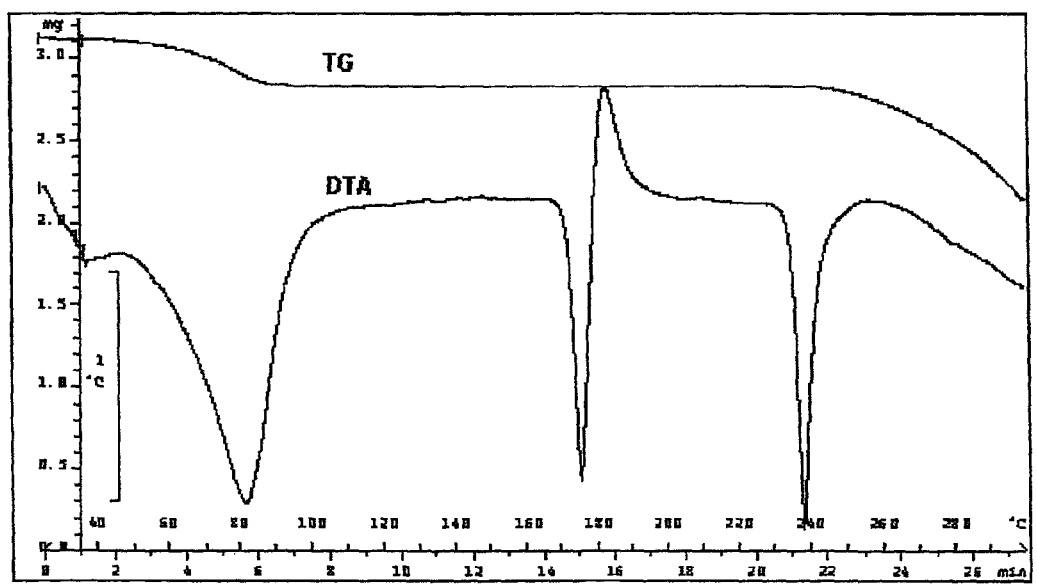
FIG. 20 shows a TG/DTA curve of monohydrobromide dihydrate.

By a method similar to that of Production Example 1, weight changes (TG) of the sample and temperature difference (DTA) from that of the standard substance were measured. The results are shown in FIG. 20.

Example 10 anhydrous (R)-3-[2-(2-hydroxymethylpyrrolidin-1-yl)ethyl]-5-methyl-2H-isoquinolin-1-one monomesylate To a solution (4 mL) of a free form (500 mg) of (R)-3-[2-(2-hydroxymethylpyrrolidin-1-yl)ethyl]-5-methyl-2H-isoquinolin-1-one in ethanol was added dropwise 2M methanesulfonic acid ethanol solution (1 mL) with stirring on an oil bath at 50° C. The bath was removed, ethyl acetate (8 mL) and seed crystals were added and the mixture was stirred to allow precipitation of crystals. After stirring under ice-cooling, the crystals were collected through filtration, washed with ethyl acetate/ethanol (2:1) and dried under reduced pressure at 50° C. for 18 hr to give the title compound (507 mg).

$^1$H-NMR

δ:1.75-2.09 (4H, m), 2.30 (3H, s), 2.49 (3H, s), 2.95-3.38 (4H, m), 3.58-3.81 (5H, m), 5.52 (1H, t, J=5 Hz), 6.55 (1H, s), 7.34 (1H, t, J=8 Hz), 7.54 (1H, d, J=7 Hz), 8.02 (1H, d, J=8 Hz), 9.23 (1H, brs), 11.42 (1H, brs)

elemental analysis $C_{17}H_{22}N_2O_2 \cdot 1MsOH$

Calculated; C: 56.52, H: 6.85, N: 7.32, S: 8.38

Found; C: 56.38, H: 6.81, N: 7.24, S: 8.26 measurement method and results of powder X-ray

Figure 21:
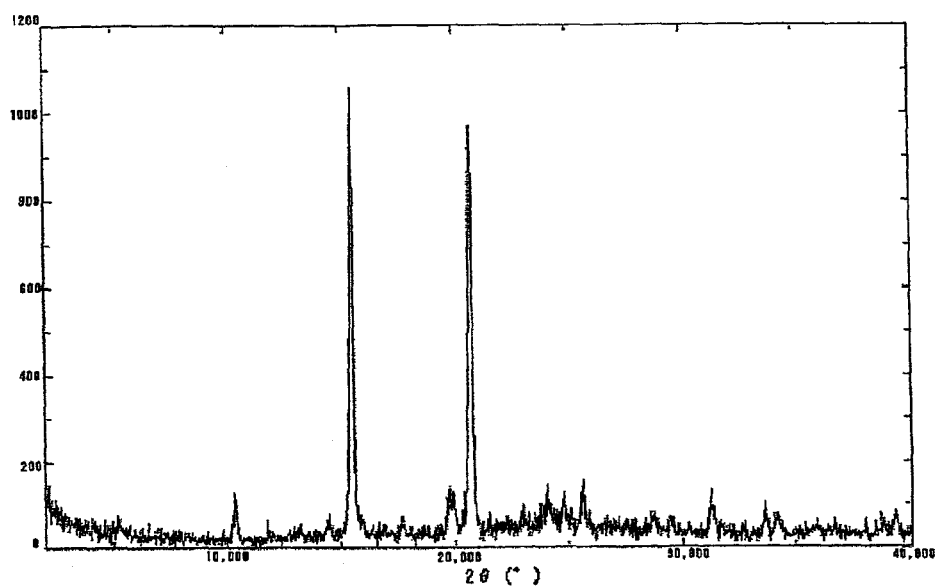
FIG. 21 shows a powder X-ray diffraction pattern of anhydrous monomesylate.

By a method similar to that of Production Example 1, powder X-ray diffraction pattern was measured. The results are shown in FIG. 21. The characteristic peaks of the crystal were at diffraction angles represented by 2θ of 15.6°, and 20.7° (±0.2°).

measurement method and results of melting point (TG/DTA)

Figure 22:
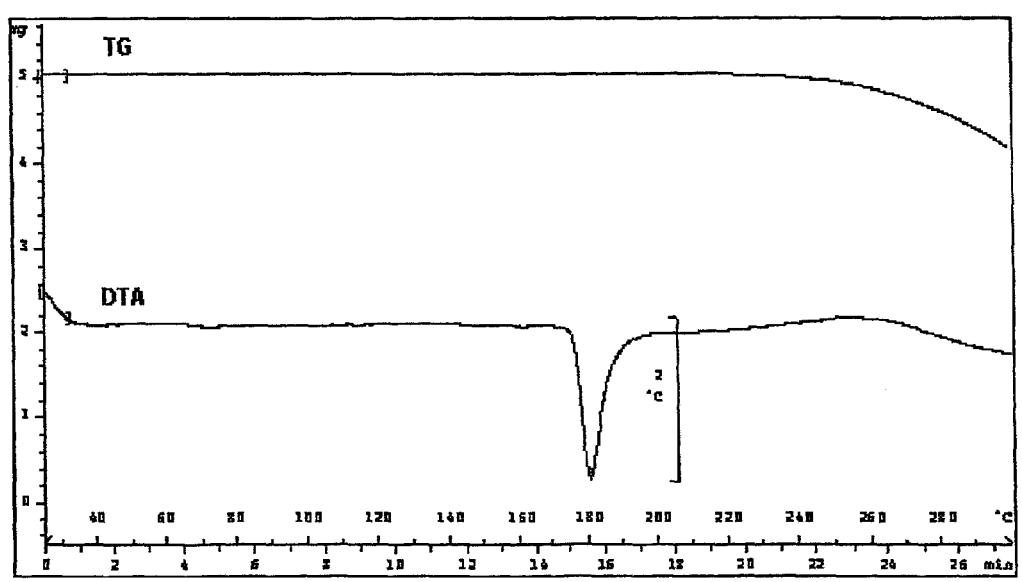
FIG. 22 shows a TG/DTA curve of anhydrous monomesylate.

By a method similar to that of Production Example 1, weight changes (TG) of the sample and temperature difference (DTA) from that of the standard substance were measured. The results are shown in FIG. 22. The melting point (extrapolated onset temperature) was 176° C.

Example 11 anhydrous (R)-3-[2-(2-hydroxymethylpyrrolidin-1-yl)ethyl]-5-methyl-2H-isoquinolin-1-one hemisulfate To a solution (7 mL) of a free form (700 mg) of (R)-3-[2-(2-hydroxymethylpyrrolidin-1-yl)ethyl]-5-methyl-2H-isoquinolin-1-one in ethanol was added dropwise 2M sulfuric acid ethanol solution (612 μL) with stirring on an oil bath at 50° C. The bath was removed, ethyl acetate (11.5 mL) and seed crystals were added with stirring at room temperature to allow precipitation of crystals. After stirring under ice-cooling, the crystals were collected through filtration, washed with ethyl acetate/ethanol (2:1) and dried under reduced pressure at 50° C. for 28 hr to give the title compound (714 mg).

$^1$H-NMR

δ:1.64-1.98 (4H, m), 2.47 (3H, s), 2.81-3.52 (9H, m), 4.97 (1H, brs), 6.49 (1H, s), 7.31 (1H, t, J=8 Hz), 7.51 (1H, d, J=7 Hz), 8.00 (1H, d, J=8 Hz), 9.47 (1H, brs), 11.39 (1H, brs)

elemental analysis $C_{17}H_{22}N_2O_2 \cdot 0.5H_2SO_4 \cdot 0.3H_2O$ (By moisture adsorption measurement, it was clarified that attached water is present around 60% of relative humidity or above, therefrom it is considered that attached water corresponding to 0.3 $H_2O$ was present in the elemental analysis measurement and the title compound is anhydrate.)

Calculated; C: 60.39, H: 6.95, N: 8.29, S: 4.74

Found; C: 60.40, H: 6.85, N: 8.21, S: 4.67 measurement method and results of powder X-ray

Figure 23:
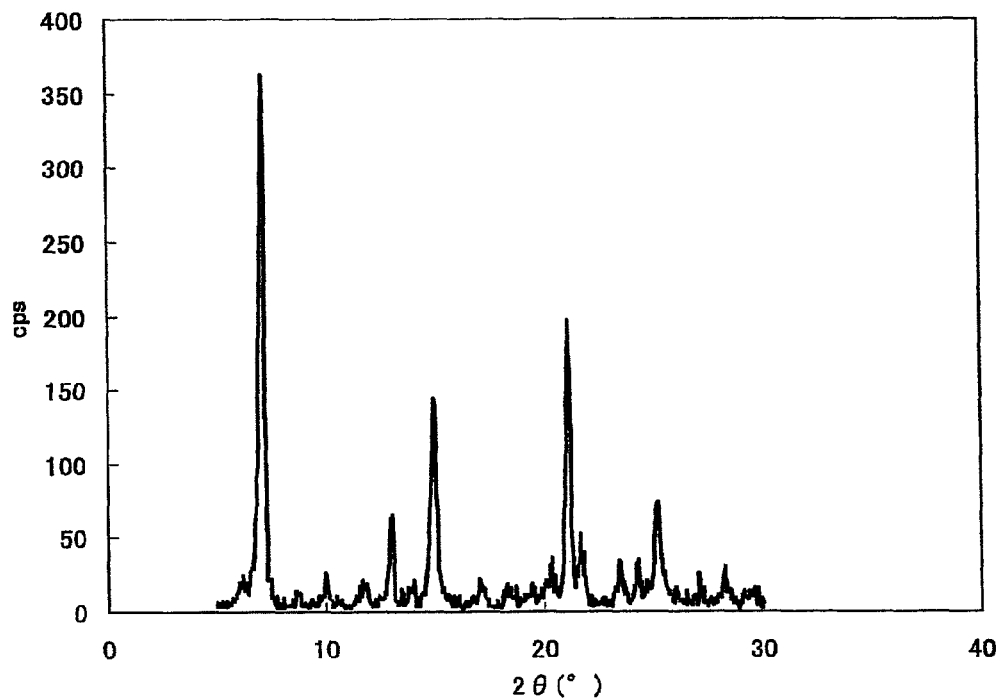
FIG. 23 shows a powder X-ray diffraction pattern of anhydrous hemisulfate.

By a method similar to that of Production Example 1, powder X-ray diffraction pattern was measured. The results are shown in FIG. 23. The characteristic peaks of the crystal were at diffraction angles represented by 2θ of 7.2°, 13.1° and 25.2° (±0.2°).

measurement method and results of melting point (TG/DTA)

Figure 24:
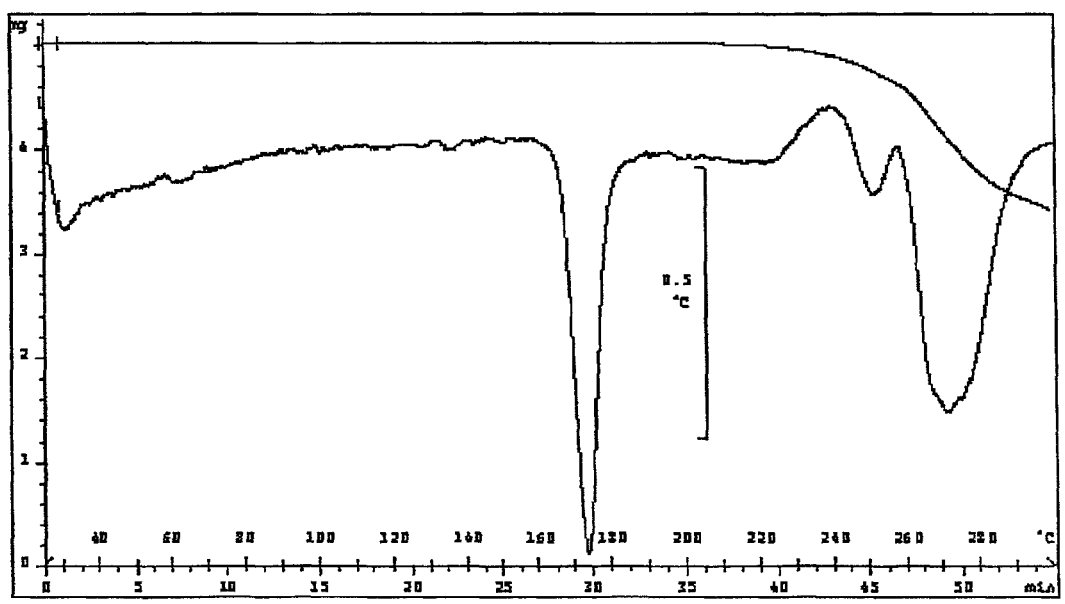
FIG. 24 shows a TG/DTA curve of anhydrous hemisulfate.

By a method similar to that of Production Example 1, weight changes (TG) of the sample and temperature difference (DTA) from that of the standard substance were measured. The results are shown in FIG. 24. The melting point (extrapolated onset temperature) was 166° C.

Example 12

(R)-3-[2-(2-hydroxymethylpyrrolidin-1-yl)ethyl]-5-methyl-2H-isoquinolin-1-one hemisulfate sesquihydrate Anhydrous (R)-3-[2-(2-hydroxymethylpyrrolidin-1-yl)ethyl]-5-methyl-2H-isoquinolin-1-one hemisulfate was preserved in a desiccator at room temperature, 75% of relative humidity for 2 days to give the title compound.

elemental analysis $C_{17}H_{22}N_2O_2 \cdot 0.5H_2SO_4 \cdot 1.6H_2O$ (By moisture adsorption measurement, it was clarified that the compound reached equilibrated state of the weight corresponding to 1.5 $H_2O$ at 10 to 90% of relative humidity, and contained a slight amount of attached water, therefrom it is considered that attached water corresponding to 0.1 $H_2O$ was present in the elemental analysis measurement and the title compound is sesquihydrate.)

Calculated; C: 56.06, H: 7.25, N: 7.69

Found; C: 55.78, H: 7.21, N: 7.52 measurement method and results of powder X-ray

Figure 25:
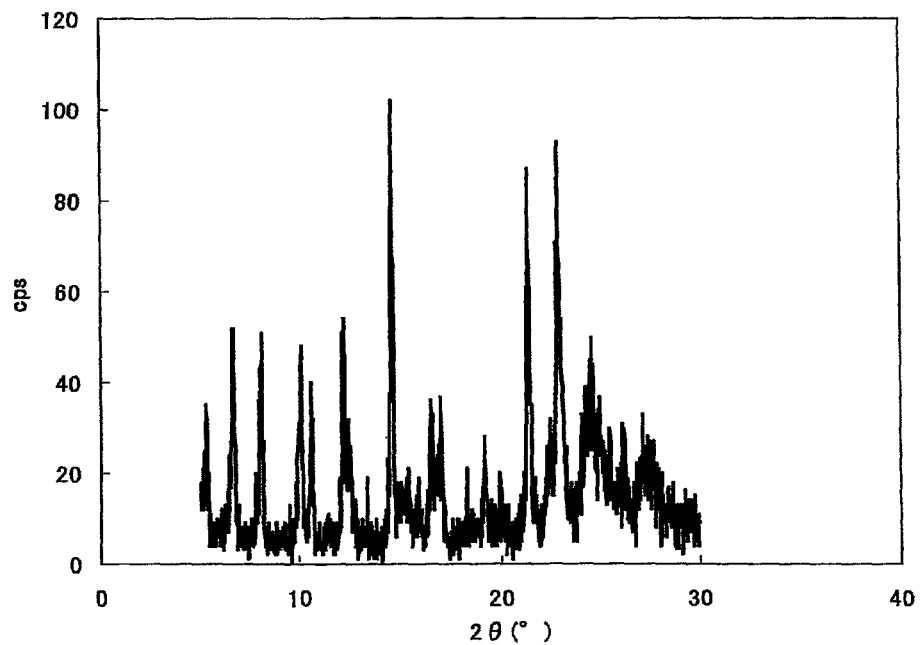
FIG. 25 shows a powder X-ray diffraction pattern of hemisulfate sesquihydrate.
Figure 26:
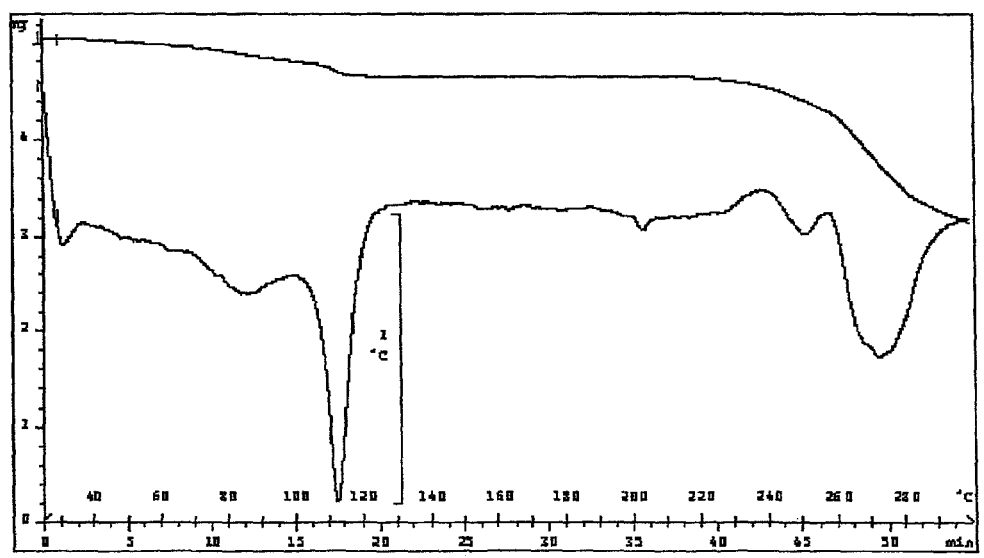
FIG. 26 shows a TG/DTA curve of hemisulfate sesquihydrate.

By a method similar to that of Production Example 1, powder X-ray diffraction pattern was measured. The results are shown in FIG. 25. The characteristic peaks of the crystal were at diffraction angles represented by 2θ of 5.3°, 8.1°, 10.6° and 22.9° (±0.2°).

measurement method and results of melting point (TG/DTA)

By a method similar to that of Production Example 1, weight changes (TG) of the sample and temperature difference (DTA) from that of the standard substance were mea-

Figure 27:
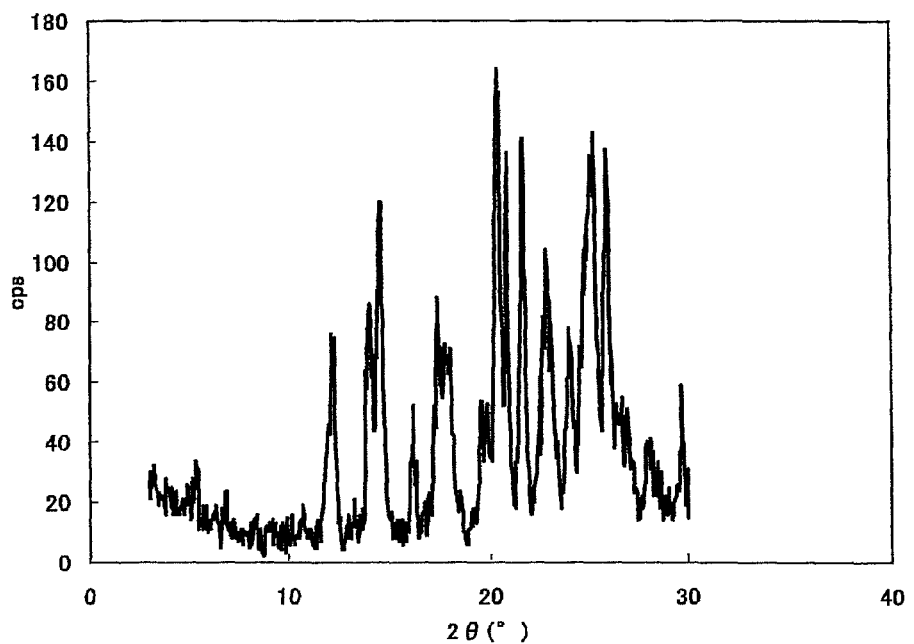
FIG. 27 shows a powder X-ray diffraction pattern of anhydrous monosulfate.
Figure 28:
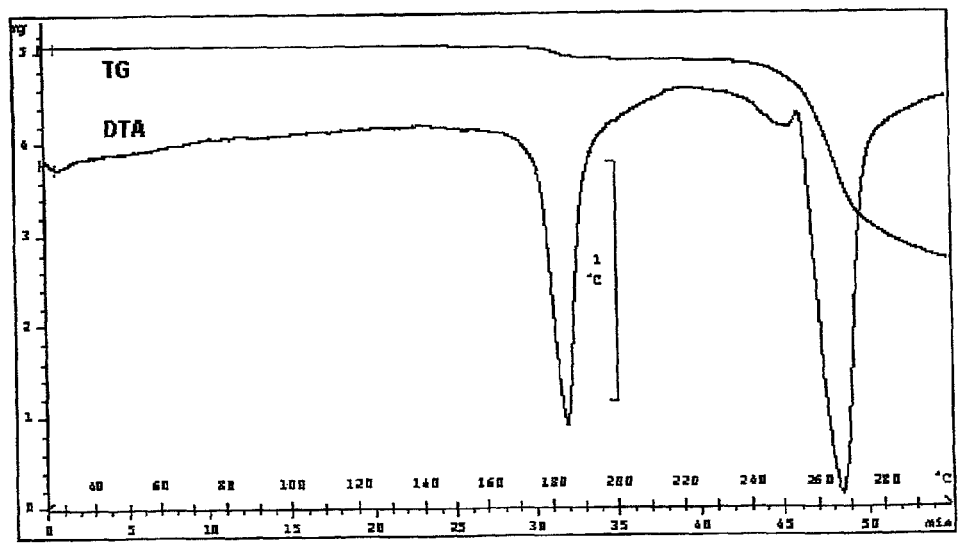
FIG. 28 shows a TG/DTA curve of anhydrous monosulfate.

Example 13 anhydrous (R)-3-[2-(2-hydroxymethylpyrrolidin-1-yl)ethyl]-5-methyl-2H-isoquinolin-1-one monosulfate To a solution (4.8 mL) of a free form (600 mg) of (R)-3-[2-(2-hydroxymethylpyrrolidin-1-yl)ethyl]-5-methyl-2H-isoquinolin-1-one in ethanol was added dropwise 2M sulfuric acid ethanol solution (1.2 mL) with stirring on an oil bath at 50° C. The bath was removed, ethyl acetate (2.4 mL) and seed crystals were added with stirring at room temperature to allow precipitation of crystals. After stirring under ice-cooling, the crystals were collected through filtration, washed with ethyl acetate/ethanol (2:1) and dried under reduced pressure at 50° C. for 18 hr to give the title compound (722 mg).
$^1$H-NMR
δ:1.74-2.12 (4H, m), 2.49 (3H, s), 2.95-3.33 (4H, m), 3.58-3.80 (5H, m), 5.50 brs), 6.55 (1H, s), 7.34 (1H, t, J=8 Hz), 7.54 (1H, d, J=7 Hz), 8.02 (1H, d, J=8 Hz), 9.23 (1H, brs), 11.42 (1H, brs)
elemental analysis
$C_{17}H_{22}N_2O_2 \cdot 1H_2SO_4$ 
Calculated; C: 53.11, H: 6.29, N: 7.29, S: 8.34
Found; C: 53.04, H: 6.19, N: 7.17, S: 8.21
measurement method and results of powder X-ray
By a method similar to that of Production Example 1, powder X-ray diffraction pattern was measured. The results are shown in FIG. 27. The characteristic peaks of the crystal were at diffraction angles represented by 2θ of 12.2° and 21.7° (±0.2°).
measurement method and results of melting point (TG/DTA)
By a method similar to that of Production Example 1, weight changes (TG) of the sample and temperature difference (DTA) from that of the standard substance were measured. The results are shown in FIG. 28. The melting point (extrapolated onset temperature) was 176° C.

Example 14

Figure 29:
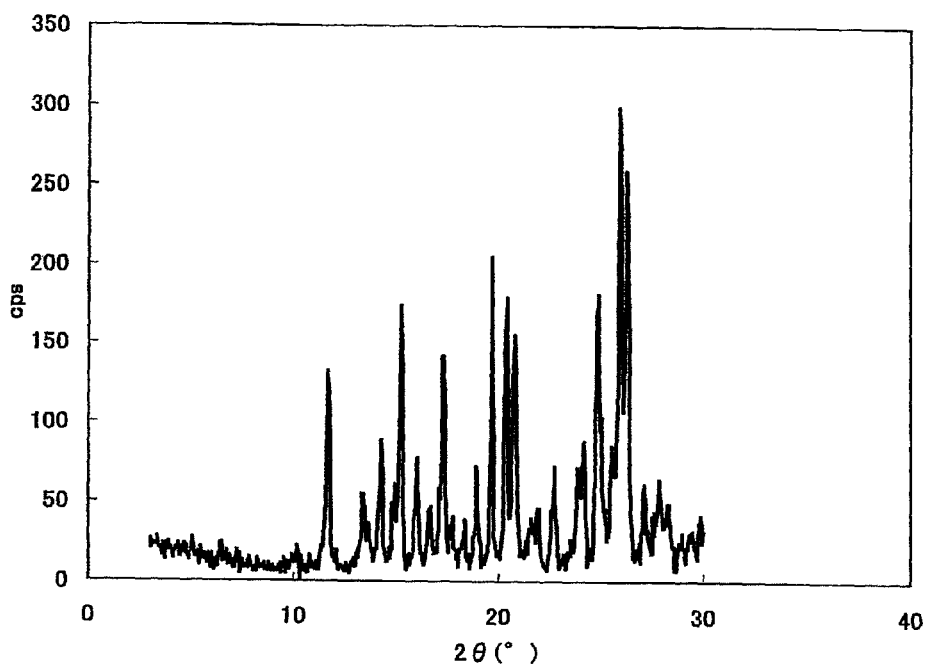
FIG. 29 shows a powder X-ray diffraction pattern of monosulfate monohydrate.
Figure 30:
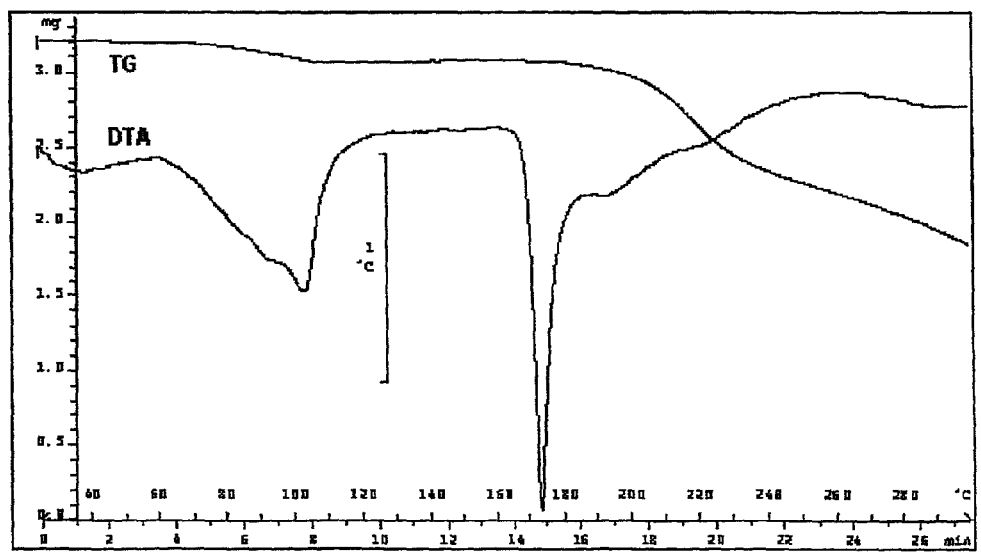
FIG. 30 shows a TG/DTA curve of monosulfate monohydrate.

(R)-3-[2-(2-hydroxymethylpyrrolidin-1-yl)ethyl]-5-methyl-2H-isoquinolin-1-one monosulfate monohydrate Anhydrous (R)-3-[2-(2-Hydroxymethylpyrrolidin-1-yl)ethyl]-5-methyl-2H-isoquinolin-1-one monosulfate was preserved in a desiccator at room temperature, 75% of relative humidity for 2 days to give the title compound.
elemental analysis
$C_{17}H_{22}N_2O_2 \cdot 1H_2SO_4 \cdot 1H_2O$
Calculated; C: 50.73, H: 6.51, N: 6.96
Found; C: 50.72, H: 6.56, N: 6.85
measurement method and results of powder X-ray
By a method similar to that of Production Example 1, powder X-ray diffraction pattern was measured. The results are shown in FIG. 29. The characteristic peaks of the crystal were at diffraction angles represented by 2θ of 11.7°, 15.2° and 19.7° (±0.2°).
measurement method and results of melting point (TG/DTA)
By a method similar to that of Production Example 1, weight changes (TG) of the sample and temperature difference (DTA) from that of the standard substance were measured. The results are shown in FIG. 30.

Example 15

Figure 31:
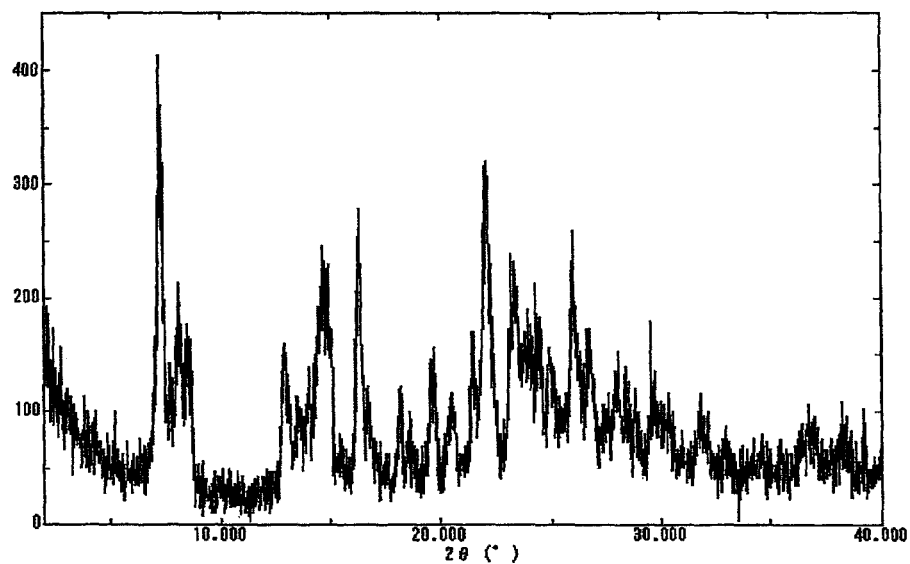
FIG. 31 shows a powder X-ray diffraction pattern of mono-D-tartrate monohydrate.
Figure 32:
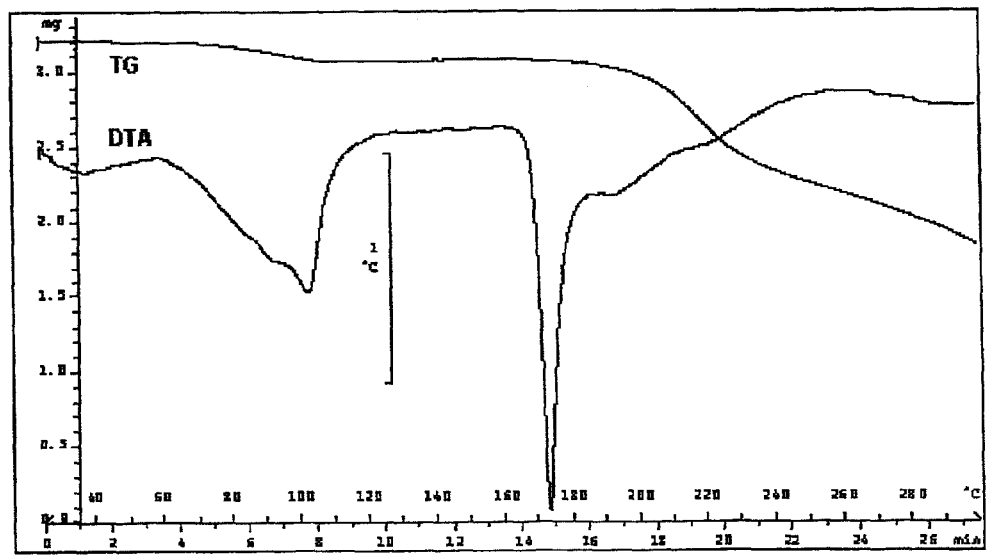
FIG. 32 shows a TG/DTA curve of mono-D-tartrate monohydrate.

(R)-3-[2-(2-hydroxymethylpyrrolidin-1-yl)ethyl]-5-methyl-2H-isoquinolin-1-one mono-D-tartrate monohydrate To a solution (500 mL) of a free form (51 mg) of (R)-3-[2-(2-hydroxymethylpyrrolidin-1-yl)ethyl]-5-methyl-2H-isoquinolin-1-one in ethanol was added dropwise 100 mg/mL D-tartaric acid ethanol solution (272 μL) under ice-cooling with stirring and the mixture was left standing for 1 hr. The resulting precipitate was collected by filtration, washed with cold ethanol (2 mL) and dried under reduced pressure at 40° C. for 4 hr to give the title compound (74 mg).
$^1$H-NMR
δ:1.59-1.94 (4H, m), 2.46 (3H, s), 2.62-2.94 (4H, m), 3.26-3.54 (5H, m), 4.11 (2H, s), 6.48 (1H, s), 7.30 (1H, t, J=8 Hz), 7.50 (1H, d, J=7 Hz), 8.00 (1H, d, J=8 Hz), 11.38 (1H, brs)
elemental analysis
$C_{17}H_{22}N_2O_2 \cdot 1C_4H_6O_6 \cdot 1H_2O$ 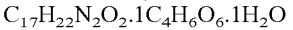
Calculated; C: 55.50, H: 6.65, N: 6.16
Found; C: 55.59, H: 6.51, N: 6.03
measurement method and results of powder X-ray
By a method similar to that of Production Example 1, powder X-ray diffraction pattern was measured. The results are shown in FIG. 31. The characteristic peaks of the crystal were at diffraction angles represented by 2θ of 8.5°, 21.1° and 22.1° (±0.2°).
measurement method and results of melting point (TG/DTA)
By a method similar to that of Production Example 1, weight changes (TG) of the sample and temperature difference (DTA) from that of the standard substance were measured. The results are shown in FIG. 32. The melting point (extrapolated onset temperature) was 169° C.

Example 16

(R)-3-[2-(2-hydroxymethylpyrrolidin-1-yl)ethyl]-5-methyl-2H-isoquinolin-1-one mono-L-tartrate monohydrate To a solution (500 μL) of a free form (52 mg) of (R)-3-[2-(2-hydroxymethylpyrrolidin-1-yl)ethyl]-5-methyl-2H-isoquinolin-1-one in ethanol was added dropwise 100 mg/mL L-tartaric acid ethanol solution (272 μL) under ice-cooling with stirring and the mixture was left standing for 1 hr. The resulting precipitate was collected by filtration, washed with cold ethanol (2 mL) and dried under reduced pressure at 50° C. for 10 hr to give the title compound (44 mg).
$^1$H-NMR
δ:1.61-1.93 (4H, m), 2.46 (3H, s), 2.60-2.89 (4H, m), 3.17-3.53 (5H, m), 4.10 (2H, s), 6.48 (1H, s), 7.30 (1H, t, J=8 Hz), 7.50 (1H, d, J=7 Hz), 8.00 (1H, d, J=8 Hz), 11.38 (1H, brs)
elemental analysis
$C_{17}H_{22}N_2O_2 \cdot 1C_4H_6O_6 \cdot 1.3H_2O$ (By moisture adsorption measurement, it was clarified that the compound reached equilibrated state of the weight corresponding to 1.0 H$_2$O at 5 to 95% of relative humidity, and contained a slight amount of attached water, therefrom it is considered that attached water corresponding to 0.3 H$_2$O was present in the elemental analysis measurement and the title compound is monohydrate.) 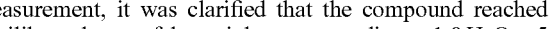
Calculated; C: 54.85, H: 6.71, N: 6.09
Found; C: 54.66, H: 6.43, N: 5.98 measurement method and results of powder X-ray

Figure 33:
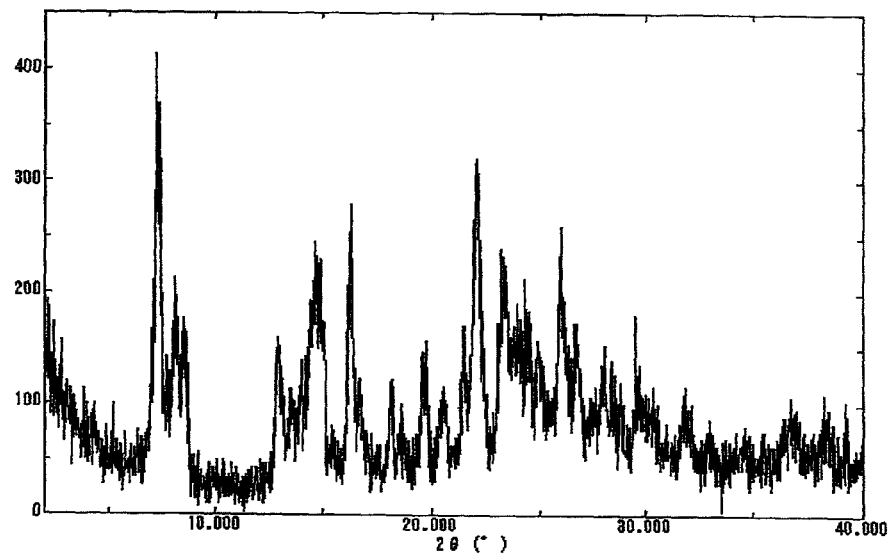
FIG. 33 shows a powder X-ray diffraction pattern of mono-L-tartrate monohydrate.

By a method similar to that of Production Example 1, powder X-ray diffraction pattern was measured. The results are shown in FIG. 33. The characteristic peaks of the crystal were at diffraction angles represented by 2θ of 7.2°, 16.2° and 22.0° (±0.2°).

measurement method and results of melting point (TG/DTA)

Figure 34:
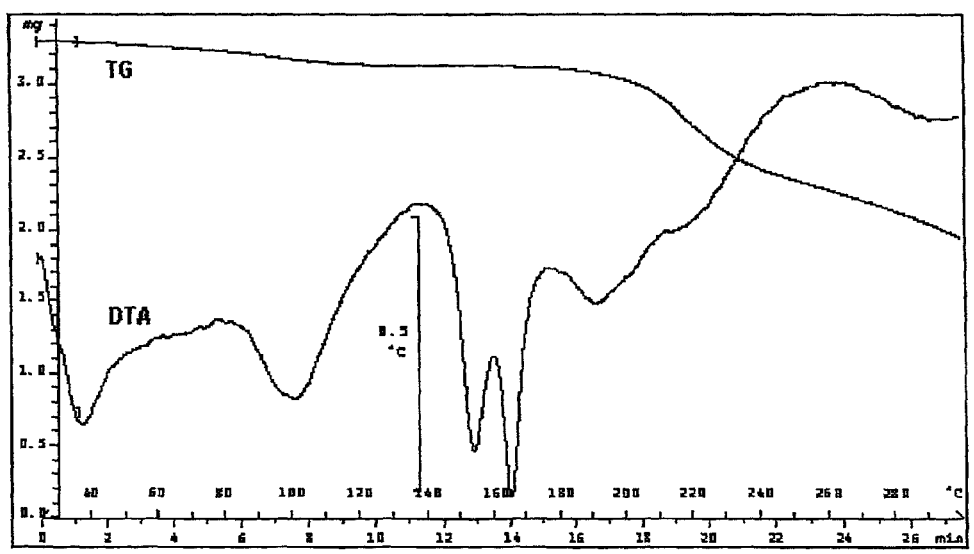
FIG. 34 shows a TG/DTA curve of mono-L-tartrate monohydrate.

By a method similar to that of Production Example 1, weight changes (TG) of the sample and temperature difference (DTA) from that of the standard substance were measured. The results are shown in FIG. 34. The melting point (extrapolated onset temperature) was 148° C.

Experimental Example 1

Chemical Stability Comparison Test of Monophosphate and Free Form

Chemical stability evaluation method: The compound (monophosphate) described in Example 1 and a free form obtained according to the method described in WO 2004/031171 were measured by 20 mg each in a weighing bottle, and preserved for one month at 30° C., 40° C., 50° C. and 40° C. at 75% of relative humidity. The sample after preservation was measured for chemical purity by HPLC. The HPLC conditions are shown below.
apparatus: SHIMADZU Corporation
column: Inertsil ODS-3V (GL Sciences Inc.) inner diameter 4.6 mm and length 150 mm
column oven: 40° C.
detection wavelength: 234 nm
measurement operation: a sample (about 1 mg) was measured in a vial container for HPLC, dissolved in a mixture (1 mL) of water/acetonitrile=1:1, and analyzed under the following conditions.
eluent composition: SOLUTION A 0.1% trifluoroacetic acid/water
SOLUTION B 0.1% trifluoroacetic acid/acetonitrile
gradient: SOLUTION B concentration: 5→100% (60 min)
mobile phase flow rate: 1.0 mL/min
injection volume: 5 μL An increase rate of related substances after one month preservation was determined from the peak area in the HPLC chromatogram. The results are shown in Table 1.

TABLE 1

| | Increase rate of related substances (%) | |
|---|---|---|
| | monophosphate | free form |
| 30° C. | −0.01 | +0.16 |
| 40° C. | −0.01 | +0.18 |
| 50° C. | −0.01 | +1.30 |
| 40° C. 75% RH | −0.02 | +0.28 |

From the above results, it was clarified that monophosphate is superior in the chemical stability as compared to the free form, and is suitable as a bulk drug for pharmaceutical products.

Experimental Example 2

Solubility Comparison Test of Monophosphate and Free Form solubility measurement method of monophosphate in water at room temperature: About 100 mg of the compound (monophosphate) described in Example 1 was measured in an Eppendorf tube, and water (100 μL) was added. This was subjected to ultrasonication on a water bath for 10 min, and gently shaken in a twin mixer (TM-282, AS ONE Corporation) at room temperature for 1 hr. After shaking, the mixture was centrifuged by a portable ultracentrifuge (10000 rpm×10 min., MC-150, TOMY SEIKO CO., LTD.) and the supernatant was filtered (Millex-LH, Millipore Corporation). The filtrate was 100-fold diluted twice with HPLC solvent (water:acetonitrile=8:2, containing 0.1% trifluoroacetic acid) to give a 10,000-fold diluted solution, which was quantified by HPLC to find the solubility of 469 mg/mL. The HPLC conditions are shown below.
apparatus: SHIMADZU Corporation
column: Inertsil ODS-3V (GL Sciences Inc.) inner diameter 4.6 mm and length 150 mm
column oven: 40° C.
detection wavelength: 234 nm
eluent composition: SOLUTION A 0.1% trifluoroacetic acid/water
SOLUTION B 0.1% trifluoroacetic acid/acetonitrile
isocratic: SOLUTION B concentration: 20% (10 min)
mobile phase flow rate: 1.0 mL/min
injection volume: 5 μL
solubility measurement method of free form in water at room temperature: A free form (1 mg) obtained according to the method described in WO 2004/031171 was measured in a sample tube, and water (1 mL) was added at room temperature. This was subjected to ultrasonication and visually confirmed to find a clear undissolved material. Therefrom it was shown that the solubility of the free form was 1 mg/mL or below.

From the above results, it was clarified that monophosphate (solubility: 469 mg/mL) has higher solubility in water than that of the free form (solubility: 1 mg/mL or below). A higher water-solubility is the advantage for the straightforward preparation of liquid pharmaceutical formulation (e.g., injection etc.). Simultaneously, moreover, it is considered to contribute to the enhancement of oral absorbability. From these, it was clarified that monophosphate has properties suitable as a bulk drug for pharmaceutical products as compared to the free form.

Experimental Example 3

Hygroscopicity Comparison Test of Monophosphate and Monohydrochloride Dihydrate

An adsorption isotherm curve measurement was performed under the following conditions.
apparatus: DVS-1 (sms Ltd., UK)
measurement temperature: 25° C.
measurement operation: a sample was measured in a sample cup, sample weight was measured by successively changing the relative humidity at 50→0→95→0→50% RH.

Figure 13:
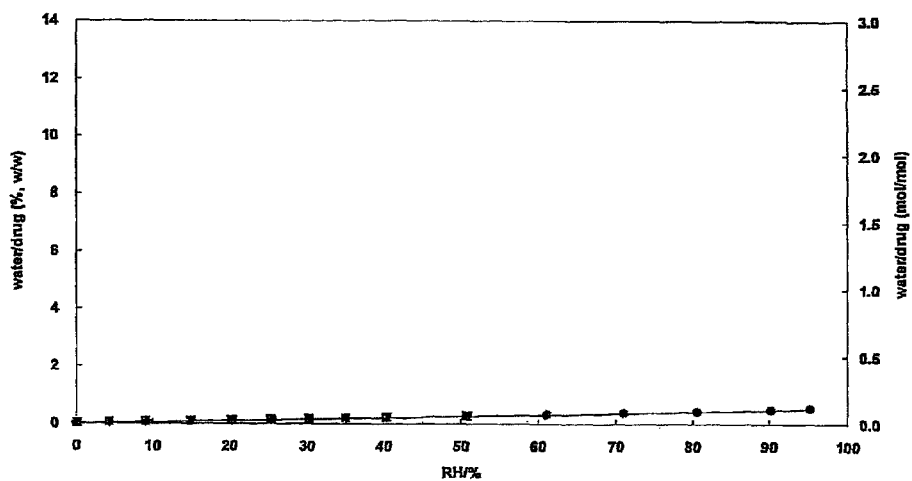
FIG. 13 shows an adsorption isotherm curve of monophosphate.
Figure 14:
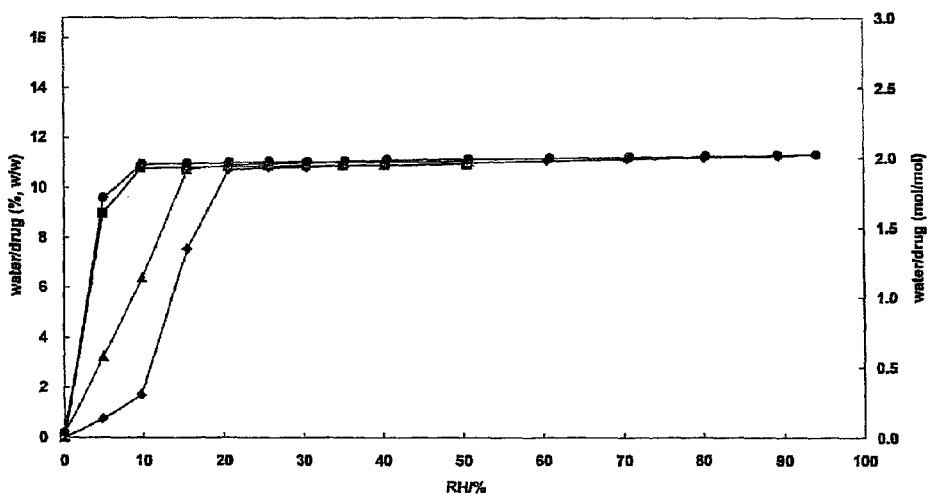
FIG. 14 shows an adsorption isotherm curve of monohydrochloride dihydrate.

The moisture absorption of the compound (monophosphate) described in Example 1 at 0-95% RH was 0.5% (w/w) (corresponding to 0.1 hydrated water, see FIG. 13). On the other hand, The moisture absorption of the compound (monohydrochloride dihydrate) described in Production Example 1 at 0-95% RH was 11% (w/w) (corresponding to 2 hydrated water, see FIG. 14), and anhydrate and dihydrate were present in mixture at 20% RH or below. It is concerned that the presence of anhydrate at 20% RH or below may cause the weighing error when weighing monohydrochloride dihydrate form. On the other hand, since monophosphate has low hygroscopicity, a measurement error due to humidity is considered to be smaller than for monohydrochloride dihydrate. The smaller weight change due to humidity is an important factor for the management of charge amount of the bulk drug for pharmaceutical products. Thus, monophosphate was clarified to have properties suitable as a bulk drug for pharmaceutical products as compared to monohydrochloride dihydrate.

Experimental Example 4

Solubility Comparison Test of Monophosphate and Monohydrochloride Dihydrate

The solubility of monophosphate in water at room temperature was 469 mg/mL as stated in Experimental Example 2. On the other hand, the solubility of monohydrochloride dihydrate in water at room temperature was 45 mg/mi when measured under the same conditions as in the solubility measurement method for monophosphate in Experimental Example 2.

From the above results, it was clarified that monophosphate possesses higher solubility in water than monohydrochloride dihydrate. For the reasons mentioned in Experimental Example 2, monophosphate was clarified to have properties suitable as a bulk drug for the novel salt, particularly a pharmaceutical product, of the present invention as compared to monohydrochloride dihydrate.

Industrial Applicability

Monophosphate is a compound which is chemically stable, has high solubility, and shows less weight change due to humidity as compared to conventionally-known free form and monohydrochloride dihydrate, and is superior as a bulk drug for pharmaceutical products.

This application is based on a patent application No. 2007-208693 filed in Japan, the contents of which are incorporated in full herein by this reference.

The invention claimed is:

1. (R)-3-[2-(2-Hydroxymethylpyrrolidin-1-yl)ethyl]-5-methyl-2H-isoquinolin-1-one monophosphate.

2. The (R)-3-[2-(2-hydroxymethylpyrrolidin-1-yl)ethyl]-5-methyl-2H-isoquinolin-1-one monophosphate according to claim 1, which is an anhydrate.

3. The (R)-3-[2-(2-hydroxymethylpyrrolidin-1-yl)ethyl]-5-methyl-2H-isoquinolin-1-one monophosphate according to claim 1, which is a crystal.

4. An anhydrous crystal of (R)-3-[2-(2-hydroxymethylpyrrolidin-1-yl)ethyl]-5-methyl-2H-isoquinolin-1-one monophosphate.

5. The crystal according to claim 4, showing a powder X-ray diffraction spectrum having a peak at a diffraction angle represented by 2θ of around)12.0° (±0.2°).

6. The crystal according to claim 4, showing a powder X-ray diffraction spectrum having a peak at a diffraction angle represented by 2θ of around) 22.8° (±0.2°).

7. The crystal according to claim 4, showing a powder X-ray diffraction spectrum having a peak at a diffraction angle represented by 2θ of around 15.0° (±0.2°).

8. The crystal according to claim 4, showing a powder X-ray diffraction spectrum having a peak at a diffraction angle represented by 2θ of around 19.6° (±0.2°).

9. The crystal according to claim 4, showing a powder X-ray diffraction spectrum having a peak at a diffraction angle represented by 2θ of around 25.8° (±0.2°).

10. The crystal according to claim 4, showing a powder X-ray diffraction spectrum having a peak at a diffraction angle represented by 2θ of around 17.8° (±0.2°).

11. The crystal according to claim 4, showing a powder X-ray diffraction spectrum having peaks at diffraction angles represented by 2θ of around 12.0°, 15.0°, 17.8°, 19.6°, 20.0°, 22.8° and 25.8° (each ±0.2°).

12. The crystal according to claim 4, having a melting point (extrapolated onset temperature) by thermogravimetry-differential thermal analysis of about 216° C. to about 217° C.

13. The crystal according to claim 4, having a melting point (extrapolated onset temperature) by thermogravimetry-differential thermal analysis of about 216° C.

14. An anhydrous crystal of (R)-3-[2-(2-hydroxymethylpyrrolidin-1-yl)ethyl]-5-methyl-2H-isoquinolin-1-one monophosphate having physicochemical properties shown by the following A and/or B:

A: having a powder X-ray diffraction pattern shown in FIG. 3,

B: having a thermogravimetry-differential thermal analysis curve shown in FIG. 4.

15. A pharmaceutical composition comprising the compound according to claim 1 and a pharmaceutically acceptable additive.

16. A poly(ADP-ribose)polymerase inhibitor comprising the compound according to claim 1 as an active ingredient.

17. A method of inhibiting the activity of a poly(ADP-ribose)polymerase, which method comprises administering an effective amount of the compound according to claim 1 to a patient, thereby inhibiting the activity of a poly(ADP-ribose)polymerase in the patient.

18. A method of treating cerebral infarction, which method comprises administering an effective amount of the compound according to claim 1 to a patient, thereby treating cerebral infarction in the patient.

19. A method of improving neurological symptoms associated with cerebral infarction, which method comprises administering an effective amount of the compound according to claim 1 to a patient, thereby improving neurological symptoms associated with cerebral infarction.

20. The method according to claim 18, wherein the cerebral infarction is an acute stage of cerebral infarction.

21. The method according to claim 19, wherein the cerebral infarction is an acute stage of cerebral infarction.

22. A pharmaceutical composition comprising the compound according to claim 4 and a pharmaceutically acceptable additive.

23. A poly(ADP-ribose)polymerase inhibitor comprising the compound according to claim 4 as an active ingredient.

24. A method of inhibiting the activity of a poly(ADP-ribose)polymerase, which method comprises administering an effective amount of the compound according to claim 4 to a patient, thereby inhibiting the activity of a poly(ADP-ribose)polymerase in the patient.

25. A method of treating cerebral infarction, which method comprises administering an effective amount of the compound according to claim 4 to a patient, thereby treating cerebral infarction in the patient.

26. A method of improving neurological symptoms associated with cerebral infarction, which method comprises administering an effective amount of the compound according to claim 4 to a patient, thereby improving neurological symptoms associated with cerebral infarction.

27. The method according to claim 25, wherein the cerebral infarction is an acute stage of cerebral infarction.

28. The method according to claim 26, wherein the cerebral infarction is an acute stage of cerebral infarction.

29. A pharmaceutical composition comprising the compound according to claim 14 and a pharmaceutically acceptable additive.

30. A poly(ADP-ribose)polymerase inhibitor comprising the compound according to claim 14 as an active ingredient.

31. A method of inhibiting the activity of a poly(ADP-ribose)polymerase, which method comprises administering an effective amount of the compound according to claim 14 to a patient, thereby inhibiting the activity of a poly(ADP-ribose)polymerase in the patient.

32. A method of treating cerebral infarction, which method comprises administering an effective amount of the compound according to claim 14 to a patient, thereby treating cerebral infarction in the patient.

33. A method of improving neurological symptoms associated with cerebral infarction, which method comprises administering an effective amount of the compound according to claim 14 to a patient, thereby improving neurological symptoms associated with cerebral infarction.

34. The method according to claim 32, wherein the cerebral infarction is an acute stage of cerebral infarction.

35. The method according to claim 33, wherein the cerebral infarction is an acute stage of cerebral infarction.

* * * * *